US010870678B2

(12) United States Patent
Levin

(10) Patent No.: US 10,870,678 B2
(45) Date of Patent: Dec. 22, 2020

(54) CHIRAL PEPTIDES

(71) Applicant: ARCUATE THERAPEUTICS, INC., Boston, MA (US)

(72) Inventor: Andrew D. Levin, Newton, MA (US)

(73) Assignee: Arcuate Therapeutics, Inc., Boston, MA (US)

( * ) Notice: Subject to any disclaimer, the term of this patent is extended or adjusted under 35 U.S.C. 154(b) by 0 days.

(21) Appl. No.: 16/092,093

(22) PCT Filed: Apr. 10, 2017

(86) PCT No.: PCT/US2017/026869
§ 371 (c)(1),
(2) Date: Oct. 8, 2018

(87) PCT Pub. No.: WO2017/180535
PCT Pub. Date: Oct. 19, 2017

(65) Prior Publication Data
US 2019/0153032 A1 May 23, 2019

Related U.S. Application Data

(60) Provisional application No. 62/321,168, filed on Apr. 11, 2016.

(51) Int. Cl.
| | |
|---|---|
| *C07K 5/107* | (2006.01) |
| *C07K 5/103* | (2006.01) |
| *C07K 5/11* | (2006.01) |
| *G01N 33/68* | (2006.01) |
| *G01N 33/92* | (2006.01) |
| *A61P 21/00* | (2006.01) |
| *A61K 38/00* | (2006.01) |

(52) U.S. Cl.
CPC ............ *C07K 5/1016* (2013.01); *A61P 21/00* (2018.01); *C07K 5/101* (2013.01); *C07K 5/1019* (2013.01); *G01N 33/68* (2013.01); *G01N 33/92* (2013.01); *A61K 38/00* (2013.01); *G01N 2500/04* (2013.01)

(58) Field of Classification Search
None
See application file for complete search history.

(56) References Cited

U.S. PATENT DOCUMENTS

| 7,718,620 B2 | 5/2010 | Szeto et al. |
| 2004/0248808 A1 | 12/2004 | Szeto et al. |

FOREIGN PATENT DOCUMENTS

| WO | 2008/154373 A1 | 12/2008 |
| WO | 2009/108695 A2 | 9/2009 |
| WO | 2009/110363 A1 | 9/2009 |
| WO | 2010/120431 A2 | 10/2010 |
| WO | 2011/019809 A1 | 2/2011 |
| WO | 2011/025734 A1 | 3/2011 |
| WO | 2011/044044 A1 | 4/2011 |
| WO | 2011082328 A1 | 7/2011 |
| WO | 2011091357 A1 | 7/2011 |
| WO | 2011/106717 A1 | 9/2011 |
| WO | 2011/139992 A1 | 11/2011 |
| WO | 2012006569 A1 | 1/2012 |
| WO | 2012/129427 A2 | 9/2012 |
| WO | 2012/174117 A2 | 12/2012 |
| WO | 2013/049697 A1 | 4/2013 |
| WO | 2013/059071 A1 | 4/2013 |
| WO | 2013/086020 A1 | 6/2013 |
| WO | 2013/126597 A1 | 8/2013 |
| WO | 2013/126775 A1 | 8/2013 |
| WO | 2013/149172 A1 | 10/2013 |
| WO | 2013/155334 A1 | 10/2013 |
| WO | 2014/022522 A1 | 2/2014 |
| WO | 2014/066419 A2 | 5/2014 |
| WO | 2014/088631 A1 | 6/2014 |
| WO | 2014/134562 A1 | 9/2014 |
| WO | 2014/165607 A2 | 10/2014 |
| WO | 2015/017781 A1 | 2/2015 |
| WO | 2015/023680 A1 | 2/2015 |
| WO | 2015/048522 A1 | 4/2015 |
| WO | 2015/048647 A1 | 4/2015 |
| WO | 2015/060462 A1 | 4/2015 |
| WO | 2015/084875 A1 | 6/2015 |
| WO | 2015/100376 A1 | 7/2015 |
| WO | 2015/130577 A2 | 9/2015 |
| WO | 2015/134096 A1 | 9/2015 |
| WO | 2016/004441 A1 | 1/2016 |

OTHER PUBLICATIONS

Birk, 2013, The Mitochondrial-Targeted Compound SS-31 Re-energizes Ischemic Mitochondria by Interacting with Cardiolipin, J Am Soc Nephrol, 24(8):1250-61.

Brown, 2014, Reduction of early reperfusion injury with the mitochondria-targeting peptide bendavia, J. Cardiovasc. Pharmacol Thep., 19:121-132.

Chen, 2011, Mitochondria-Targeted Peptide MTP-131 Alleviates Mitochondrial Dysfunction and Oxidative Damage in Human Trabecular Meshwork Cells, Invest Ophthalmol Vis Sci., 52(10):7027-7037.

Shimoyama, 2012, Superior Analgesic Effect of H-Dmt-D-Arg-Phe-Lys-NH2 ([Dmt1] DALDA), a Multifunctional Opioid Peptide, Compared to Morphine in a Rat Model of Neuropathic Pain, Chemical Biology and Drug Design, Chem Biol Drug Des., 80(5):771-4.

Stealth Biotherapeutics Inc., A Multiple Ascending Dose Study to Evaluate the Safety, Tolerability, Pharmacokinetics and Efficacy of Bendavia™ (MTP-131) in Patients With Heart Failure, ClinicalTrials.gov Identifier: NCT02388529, Mar. 17, 2015, U.S. National Library of Medicine (6 pages).

Stealth Biotherapeutics Inc., A Phase 1 Study Examining the Pharmacokinetics and Tolerability of a Single Oral Dose of Bendavia (MTP-131), ClinicalTrials.gov Identifier: NCT01754818, Dec. 21, 2012, U.S. National Library of Medicine (8 pages).

(Continued)

*Primary Examiner* — Christina Bradley
(74) *Attorney, Agent, or Firm* — Brown Rudnick LLP

(57) ABSTRACT

The present disclosure provides certain chiral peptide agents, and uses relating thereto.

14 Claims, 5 Drawing Sheets

(56) References Cited

OTHER PUBLICATIONS

Stealth Biotherapeutics Inc., A Phase 2 Study to Evaluate the Impact of MTP-131 (Bendavia™) on Skeletal Muscle Function in Elderly (MOTION), ClinicalTrials.gov Identifier: NCT02245620, Sep. 19, 2014, U.S. National Library of Medicine (5 pages).

Stealth Biotherapeutics Inc., A Study Investigating the Safety, Tolerability, and Efficacy of MTP-131 for the Treatment of Mitochondrial Myopathy (MMPOWER), ClinicalTrials.gov Identifier: NCT02367014, Feb. 20, 2015, U. S. National Library of Medicine (6 pages).

Stealth Biotherapeutics Inc., A Study Investigating the Safety, Tolerability, and Pharmacokinetics of MTP-131 in Subjects With Congestive Heart Failure, ClinicalTrials.gov Identifier: NCT02388464, Mar. 17, 2015, U.S. National Library of Medicine (6 pages).

Stealth Biotherapeutics Inc., Evaluation of Myocardial Effects of Bendavia for Reducing Reperfusion Injury in Patients With Acute Coronary Events (EMBRACE), NCT01572909, Apr. 6, 2012, U.S. National Library of Medicine (11 pages).

Stealth Biotherapeutics Inc., Safety and Pharmacokinetic (PK) Study of Oral Bendavia Administered for 7 Days, ClinicalTrials.gov Identifier: NCT01786915, Feb. 8, 2013, U.S. National Library of Medicine (8 pages).

Stealth Biotherapeutics Inc., Study to Assess the Effects of Intravenous Bendavia in Patients Undergoing Percutaneous Transluminal Angioplasty of the Renal Artery (PTRA) (EVOLVE), ClinicalTrials.gov Identifier: NCT01755858, Dec. 24, 2012, U.S. National Library of Medicine (11 pages).

Stealth Biotherapeutics Inc., Study to Assess the Pharmacodynamic Effects of Unfractionated Heparin (UFH) in Healthy Volunteers With and Without Bendavia, ClinicalTrials.gov Identifier: NCT01513200, Jan. 20, 2012, U.S. National Library of Medicine (7 pages).

Stealth Biotherapeutics Inc., Study to Evaluate Safety, Tolerability, and Pharmacokinetics (PK) of Intravenous (IV) Infusion of MTP-131 (Bendavia™) in Healthy Adults, ClinicalTrials.gov Identifier: NCT01115920, May 4, 2010, U.S. National Library of Medicine (6 pages).

Stealth Biotherapeutics Inc., The Impact of Intravenous Bendavia™ on Endothelial Reactivity Dysfunction in Cigarette Smoking, ClinicalTrials.gov Identifier: NCT01518985, Jan. 26, 2012, U.S. National Library of Medicine (6 pages).

Translation of WO2009110363 retrieved from Espacenet on Dec. 11, 2018 (11 pages).

ical filing date Apr. 10, 2017, which claims priority to U.S.
CHIRAL PEPTIDES

CROSS-REFERENCE TO RELATED APPLICATIONS

This application is a U.S. national stage entry of International Application No. PCT/US2017/026869, with international filing date Apr. 10, 2017, which claims priority to U.S. provisional application Ser. No. 62/321,168, filed Apr. 11, 2016, the contents of each of which are hereby incorporated herein by reference.

BACKGROUND

Many diseases are related to mitochondria function. There is need to treat such diseases.

SUMMARY

Mitochondria exist in virtually all eukaryotic cells, and are essential to cell survival by producing adenosine triphosphate (ATP) via oxidative phosphorylation. Mitochondrial dysfunction, including ATP hydrolysis and $Ca^{2+}$ overload, causes mitochondrial permeability transition (MPT). MPT is characterized by uncoupling of oxidative phosphorylation, loss of mitochondrial membrane potential, increased permeability of the inner membrane, and swelling, all of which can lead to cell death. Thus, there is a need to inhibit MPT in conditions such as ischemia-reperfusion, hypoxia, hypoglycemia, and other diseases and conditions, which result in pathological changes as a result of the permeability of transitioning of the mitochondrial membranes. Such diseases and conditions include many of the common neurodegenerative diseases.

Moreover, there is a need to improve mitochondria function to increase reserve capacity to better tolerate cellular stress in the form of reactive oxygen species (ROS). Such methods that increase reserve capacity while maintaining oxygen consumption rates may prove useful in the treatment or prevention of such mitochondria-associated diseases, disorders, or conditions.

The present invention provides peptide agents particularly useful in improving mitochondria function by, for example, increasing reserve capacity while maintaining oxygen consumption rate. The present disclosure encompasses the recognition that peptide agents described herein are particularly useful for treating or preventing various diseases that are related to mitochondria function. In some embodiments, the present disclosure provides technologies, e.g., compounds, compositions, methods, etc., relating to peptide agents for treatment or prevention of various diseases, for example, diseases associated with mitochondria function.

In some embodiments, a peptide agent for use in accordance with the present disclosure is one that binds a component of the inner mitochondrial membrane, e.g., cardiolipin. The present invention provides an insight that, in some instances, a peptide with multiple cationic moieties, for example 2 cationic moieties, configured appropriate may bind cardiolipin. Furthermore, the present invention also provides an insight that, in some instances, chiral character of peptide agents described herein may be as important as or more important than amino acid sequence. In some embodiments, each cationic moiety is spatially arranged in the same direction (e.g., up or down) with respect to the peptide backbone. Additionally or alternatively, in some embodiments, each remaining moiety (e.g., hydrophobic moiety) is spatially arranged in the same direction (e.g., up or down) with respect to the peptide backbone, opposite to the cationic moieties.

In some embodiments, a provided peptide agent has a structure of formula I:

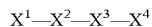

wherein:
$X^1$ is the N-terminal amino acid and $X^4$ is the C-terminal amino acid;
and further wherein:
$X^1$ comprises an N-terminal moiety selected from $-N(R)_2$ or $-N(R)-C(O)-R$;
$X^4$ comprises a C-terminal moiety selected from $-C(O)OR$ or $-C(O)N(R)_2$;
each R is independently hydrogen or optionally substituted $C_{1-6}$ aliphatic;
and further wherein:
either:
$X^2$ and $X^4$ are cationic amino acids; or
$X^1$ and $X^3$ are cationic amino acids,
and further wherein:
  $X^1$ is an L-amino acid, and each of $X^2$, $X^4$, and $X^4$ is a D-amino acid;
  $X^2$ is an L-amino acid, and each of $X^1$, $X^3$, and $X^4$ is a D-amino acid;
  $X^4$ is a D-amino acid, and each of $X^1$, $X^2$, and $X^3$ is an L-amino acid;
  each of $X^1$, $X^2$, and $X^3$ is a D-amino acid, and $X^4$ is an L-amino acid;
  each of $X^1$ and $X^2$ is a D-amino acid, and each of $X^3$ and $X^4$ is an L-amino acid;
  each of $X^1$ and $X^2$ is an L-amino acid, and each of $X^3$ and $X^4$ is a D-amino acid;
  $X^3$ is a D-amino acid, and each of $X^1$, $X^2$, and $X^4$ is an L-amino acid;
  $X^3$ is a L-amino acid, and each of $X^1$, $X^2$, and $X^4$ is a D-amino acid;
  each of $X^1$ and $X^4$ is an L-amino acid, and each of $X^2$ and $X^3$ is a D-amino acid;
  each of $X^1$ and $X^4$ is an D-amino acid, and each of $X^2$ and $X^3$ is an L-amino acid;
  each of $X^1$ and $X^3$ is an L-amino acid, and each of $X^2$ and $X^4$ is a D-amino acid;
  each of $X^1$ and $X^3$ is an D-amino acid, and each of $X^2$ and $X^4$ is an L-amino acid;
  each of $X^1$, $X^2$, $X^3$, and $X^4$ is a D-amino acid; or
  each of $X^1$, $X^2$, $X^3$, and $X^4$ is an L-amino acid.

In some embodiments, the present invention provides a method for reducing oxidative damage in a subject in need thereof, the method comprising administering to the subject an effective amount of one or more peptide agents described herein.

In another embodiment, the present invention provides a method for reducing the number of mitochondria undergoing mitochondrial permeability transitioning (MPT), or preventing mitochondrial permeability transitioning in a mammal in need thereof, the method comprising administering to the mammal an effective amount of one or more aromatic cationic peptides.

DEFINITIONS

A. Chemical Definitions

Figure 1:
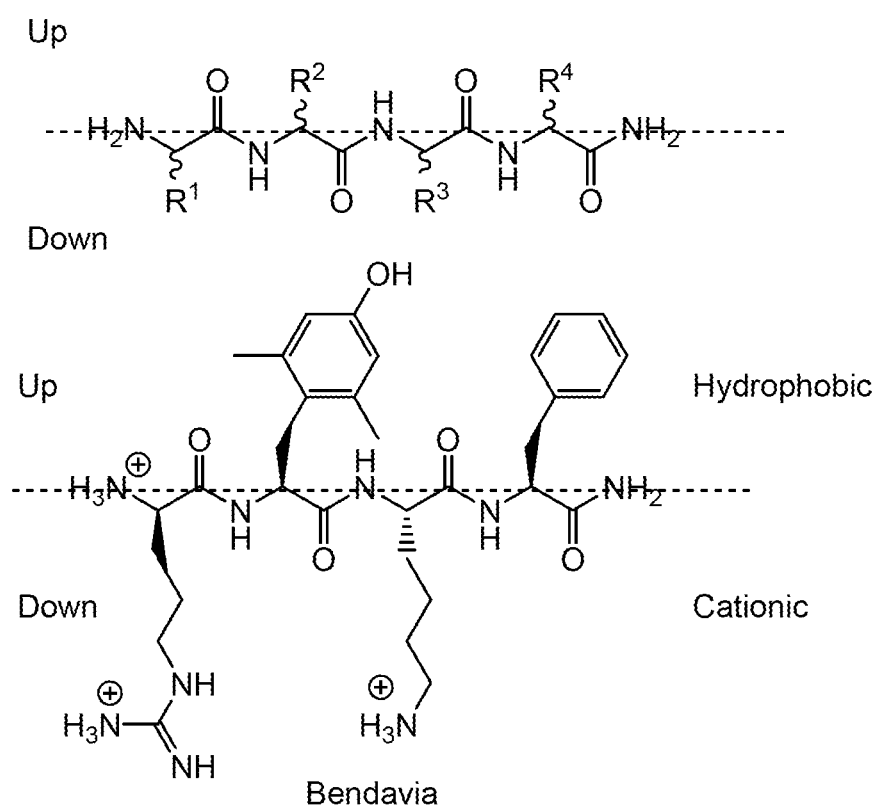
FIG. 1. Spatial configuration of Bendavia.

As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Aliphatic: As used herein, "aliphatic" means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or polycyclic hydrocarbon that is completely saturated or that contains one or more units of unsaturation that has a single point of attachment to the rest of the molecule. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkenyl: As used herein, the term "alkenyl" refers to an alkyl group, as defined herein, having one or more double bonds.

Alkynyl: As used herein, the term "alkynyl" refers to an alkyl group, as defined herein, having one or more triple bonds.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents include halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°\ C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR—$, SC(S)SR°; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; —$SiR°_3$; —$OSiR°_3$; —$(C_{1-4}$ straight or branched)alkylene)O—N(R°)_2$; or —$(C_{1-4}$ straight or branched) alkylene)C(O)O—N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —SSR$^•$ wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O—$, or —$S(C(R^*_2))_{2-3}S—$, wherein each independent occurrence of R. is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R. include halogen, —$R^•$, -(haloR$^•$), —OH, —$OR^•$, —O(haloR$^•$), —CN, —C(O)OH, —C(O)OR$^•$, —$NH_2$, —NHR$^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

In some embodiments, suitable substituents on a substitutable nitrogen include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

B. Other Definitions

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent" may be used to refer to a compound or entity of any chemical class including, for example, a polypeptide, nucleic acid, saccharide, lipid, small molecule, metal, or combination thereof. Those of ordinary skill in the art will appreciate that, in general, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer. In some embodiments, the term may refer to a compound or entity that lacks or is substantially free of any polymeric moiety Agonist: Those skilled in the art will appreciate that the term "agonist" may be used to refer to an agent condition, or event whose presence, level, degree, type, or form correlates with increased level or activity of another agent (i.e., the agonized agent). In general, an agonist may be or include an agent of any chemical class including, for example, small molecules, polypeptides, nucleic acids, carbohydrates, lipids, metals, and/or any other entity that shows the relevant activating activity. In some embodiments, an agonist may be direct (in which case it exerts its influence directly upon its target); in some embodiments, an agonist may be indirect (in which case it exerts its influence by other than binding to its target; e.g., by interacting with a regulator of the target, so that level or activity of the target is altered).

Amino acid: in its broadest sense, refers to any compound and/or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, a nonstandard amino acid refers to those that may result in a modified peptide backbone. For example, in some embodiments, a nonstandard amino acid is selected from an N-Me-amino acid, α-hydroxy acids, and N-substituted glycines. In some embodiments, a nonstandard amino acid is selected from:

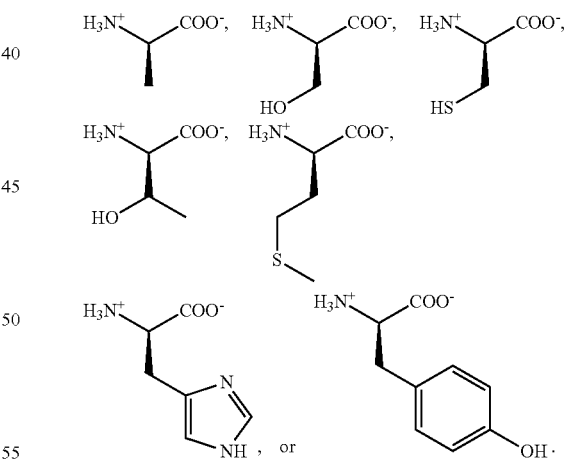

In some embodiments, a nonstandard amino acid is selected from:

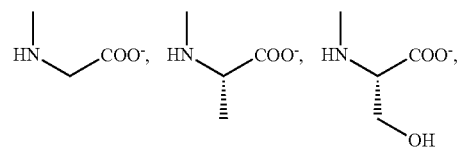

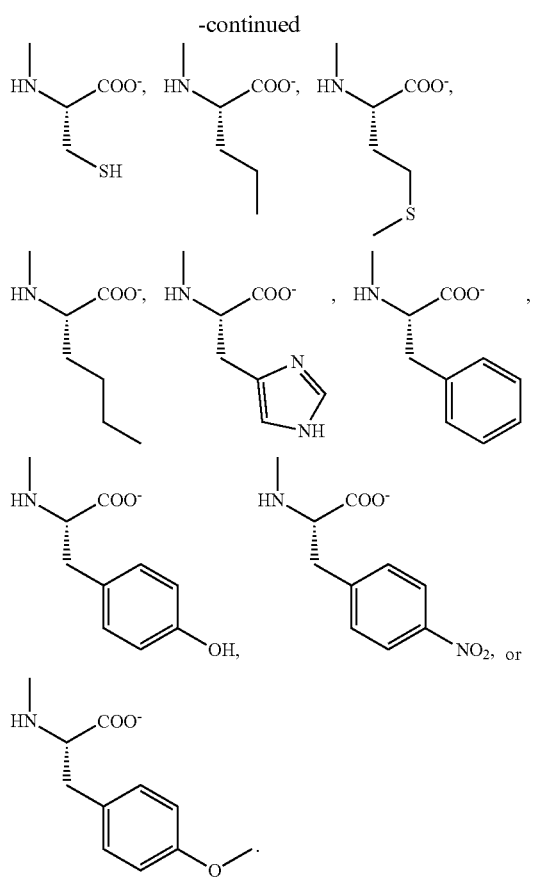
In some embodiments, a nonstandard amino acid is selected from:
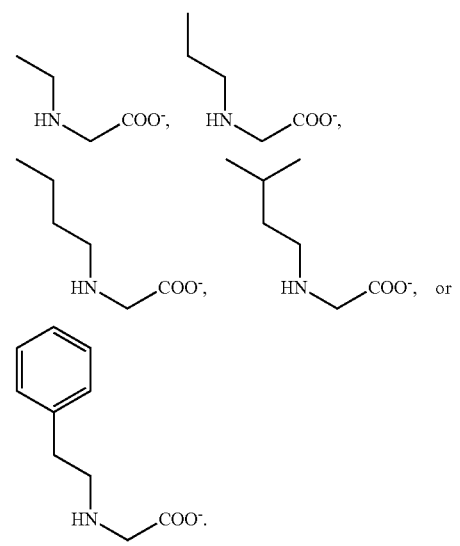
In some embodiments, a nonstandard amino acid is selected from:
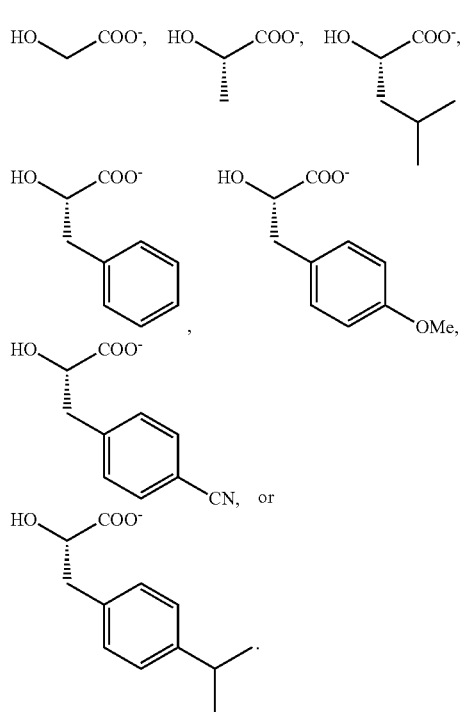
In some embodiments, a nonstandard amino acid is selected from:
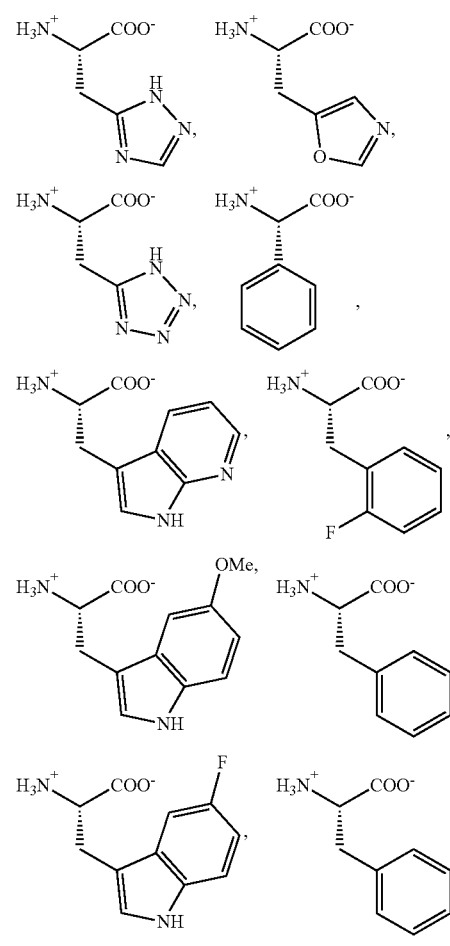

-continued

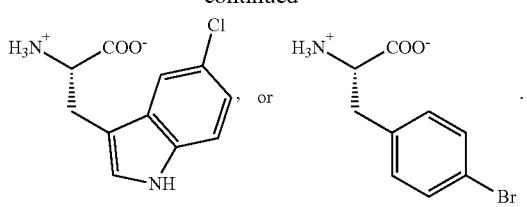

In some embodiments, a nonstandard amino acid is selected from:

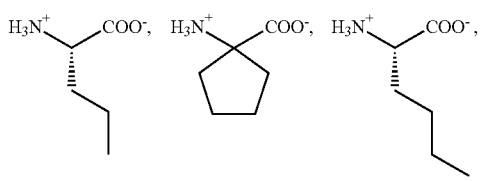

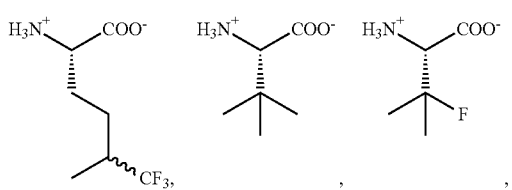

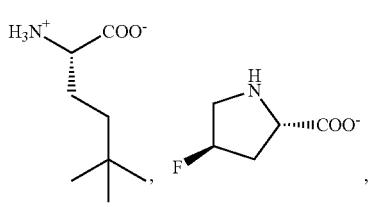

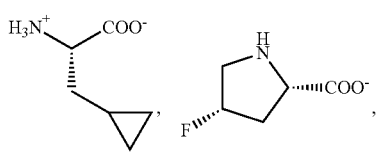

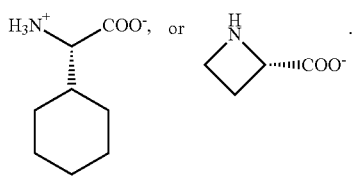

In some embodiments, a nonstandard amino acid is selected from:

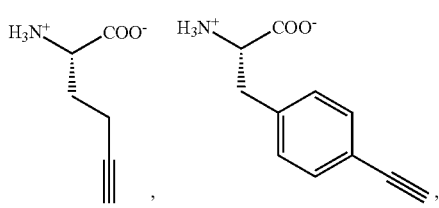

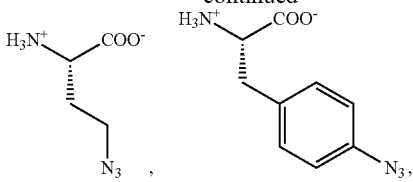

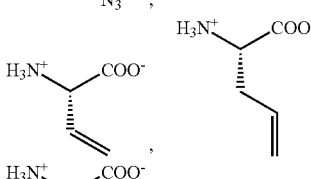

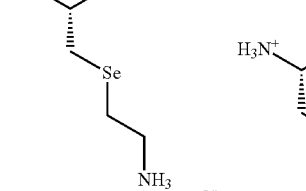

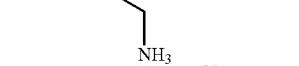

In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

In some embodiments, an amino acid is a cationic amino acid. "Cationic amino acid" refers to any amino acid that comprises positive charge. Non-limiting examples of cationic amino acids include L- and D-configurations of arginine, histidine, lysine, ornithine, α,β-diaminopropionic acid (Dap), α,γ-diaminobutyric acid (Dab), 2-amino-3-guanidinopropionic acid, citrulline, or hydroxylysine. In some embodiments, a cationic amino acid, including a carboxy- and/or amino-terminal amino acid in a polypeptide, can contain a structural modification as compared with the general structure above. For example, in some embodiments, a cationic amino acid may be modified by methylation, amidation, acetylation, and/or substitution as compared with the general structure.

In some embodiments, an amino acid is an anionic amino acid. "Anionic amino acid" refers to any amino acid that comprises negative charge. Non-limiting examples of anionic amino acids include both L- and D-configurations of aspartic acid glutamic acid, 2,6-diaminopimelic acid, α-aminosuberic acid, or α-aminoadipic acid. In some embodiments, an anionic amino acid, including a carboxy- and/or amino-terminal amino acid in a polypeptide, can contain a structural modification as compared with the general structure above. For example, in some embodiments, an anionic amino acid may be modified by methylation, amidation, acetylation, and/or substitution as compared with the general structure.

In some embodiments, an amino acid is a hydrophobic amino acid. "Hydrophobic amino acid" refers to any amino acid that comprises a hydrophobic moiety. Non-limiting examples of hydrophobic amino acids include both L- and D- configurations of glycine, proline, alanine, valine, isoleucine, leucine, methionine, phenylalanine, tryptophan, 2-aminobutyric acid (Abu), α-aminoisobutyric acid (Aib), cyclohexylalanine (Cha), 2-naphthylalanine (Nal), 3,3-diphenylalanine, 3-(2-pyridyl)-alanine, 3-(3-pyridyl)-alanine, 3-(4-pyridyl)-alanine, 3-(2-quinolyl)-alanine, 3-(3-quinolyl)-alanine, 3-(4-quinolyl)-alanine, 3-(2-quinoxalyl)-alanine, β-(4-thiazolyl)-alanine, β-(2-thienyl)-alanine, β-(3-thienyl)-alanine, 3-cyclopentyl-alanine, β-(2-furyl)-alanine, 2-(7-octenyl)-alanine, 2-pentenyl-alanine, 2-(4-pentenyl)-alanine, propargyl-alanine, 2-(2-propenyl)-alanine, (3-indolylacetyl)-alanine, 3-(1-pyrazolyl)-alanine, allylglycine, cyclohexylglycine (Chg), cyclopropylglycine, phenylglycine (Phg), fluorophenylglycine, 4-fluorophenylglycine, (2-indanyl)-glycine, propargylglycine, 2-thienylglycine, 3-thienylglycine, 2-(4-trifluoromethyl-phenyl)-glycine, 2-chlorophenylglycine, neopentylglycine, cycloleucine, t-butylglycine, t-leucine, 5,5,5-trifluoro-leucine, norleucine (Nle), norvaline (Nva), or 4-hydroxyphenylglycine. In some embodiments, a hydrophobic amino acid, including a carboxy- and/or amino-terminal amino acid in a polypeptide, can contain a structural modification as compared with the general structure above. For example, in some embodiments, a hydrophobic amino acid may be modified by methylation, amidation, acetylation, and/or substitution as compared with the general structure.

In some embodiments, an amino acid is a hydrophilic or polar amino acid. "Hydrophilic amino acid" refers to any amino acid that comprises a hydrophilic moiety. "Polar amino acid" refers to any amino acid that comprises a dipole. Non-limiting examples of hydrophilic and/or polar amino acids include both L- and D- configurations of serine, threonine, asparagine, glutamine, cysteine, selenocysteine, citrulline, thiocitrulline, tyrosine, O-methyl-tyrosine, or 2,6-dimethyltyrosine (Dmt). In some embodiments, a hydrophilic amino acid, including a carboxy- and/or amino-terminal amino acid in a polypeptide, can contain a structural modification as compared with the general structure above. For example, in some embodiments, a hydrophilic amino acid may be modified by methylation, amidation, acetylation, and/or substitution as compared with the general structure.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Combination therapy: As will be understood by those skilled in the art, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens. In some embodiments, "administration" of combination therapy may involve administration of one or more agents to a subject receiving the other agents in the combination. For clarity, combination therapy does not require that individual agents be administered together in a single composition (or even necessarily at the same time), although in some embodiments, two or more active agents, entities, or moieties may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Intraperitoneal: The phrases "intraperitoneal administration" and "administered intraperitoneally" as used herein have their art-understood meaning referring to administration of a compound or composition into the peritoneum of a subject.

Mitochondrial reserve capacity: As cells are subjected to stress, mitochondria have the ability to increase ATP production above their basal functioning levels, which is available to serve the increased energy demands for, e.g., maintenance of organ function, cellular repair, or detoxification of reactive species.

Moiety: Those skilled in the art will appreciate that a "moiety" is a defined chemical group or entity with a particular structure and/or or activity, as described herein.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Subject: As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Predetermined: By predetermined is meant deliberately selected, for example as opposed to randomly occurring or achieved.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present disclosure. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the disclosure, chemical compositions may be provided that are or include pure preparations of a single tautomeric form of a compound. In some embodiments, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the disclosure, chemical compositions may contain all tautomeric forms of a compound. In some embodiments of the disclosure, chemical compositions may contain less than all tautomeric forms of a compound. In some embodiments of the disclosure, chemical compositions may contain one or more tautomeric forms of a compound in amounts that vary over time as a result of interconversion. In some embodiments of the disclosure, the tautomerism is keto-enol tautomerism. One of skill in the chemical arts would recognize that a keto-enol tautomer can be "trapped" (i.e., chemically modified such that it remains in the "enol" form) using any suitable reagent known in the chemical arts in to provide an enol derivative that may subsequently be isolated using one or more suitable techniques known in the art. Unless otherwise indicated, the present disclosure encompasses all tautomeric forms of relevant compounds, whether in pure form or in admixture with one another.

Tetrapeptide: As used herein, the phrase "tetrapeptide," typically refers to a compound whose structure contains four amino acid residues attached to one another by a peptide bond. In some embodiments, one or more of the amino acids is a nonstandard amino acid. In some embodiments, all of the amino acids may be nonstandard amino acids. In some embodiments, one or more of the amino acids is a standard amino acid. In some embodiments, all of the amino acids may be standard amino acids. In some embodiments, a nonstandard amino acid may have a structure that differs from the canonical amino acid structure, but nonetheless is capable of forming one or more peptide bonds. In some embodiments, a tetrapeptide agent as described herein may have a structure that includes one or more terminal moieties in addition to the amino acid residues and/or one or more other pendant moieties covalently associated with the tetrapeptide.

Therapeutic agent: As used herein, the phrase "therapeutic agent" refers to an agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

DETAILED DESCRIPTION OF CERTAIN EMBODIMENTS

Bendavia

It has been shown that certain aromatic-cationic peptides, preferably tetrapeptides of DLLL chirality and most preferably Bendavia (D-Arg-Dmt-Lys-Phe-NH$_2$), significantly reduce the number of mitochondria undergoing, or even completely preventing, mitochondrial reserve capacity (MPT). See, for example, US 2004/0248808 and U.S. Pat. No. 7,718,620, and references cited therein, the entirety of each of which is incorporated herein by reference. Reducing the number of mitochondria undergoing and preventing MPT can have a variety of benefits; MPT is reported to be associated with several common diseases and conditions in humans and mammals. See, for example, WO2008/154373A1, WO2009/110363A1, WO2009/108695A1, WO2011/019809A1, WO2011/044044A1, WO2011/106717A1, WO2011/025734A1, WO2011082328A1, WO2012006569A1, WO2013/126597A1, WO2013/149172A1, WO2013/126775A1, WO2014/022522A1, WO2014066419A1, WO2014/134562A1, WO2015/017781A1, WO2015/023680A1, WO2015/084875A1, WO2015/130577A1, WO2015/048522A1, WO2015/048647A1, and WO2016/004441A1, the entirety of which have been incorporated by reference.

Bendavia has also been shown to prevent both immortalized human trabecular meshwork (iHTM) and glaucomatous human trabecular meshwork (GTM$_3$) cells from sustain oxidative stress induced by H$_2$O$_2$. (Chen M, Liu B, Gao, Q, Zhuo, Y, Ge, J (September 2011). "Mitochondria-Targeted Peptide MTP-131 Alleviates Mitochondrial Dysfunction and Oxidative Damage in Human Trabecular Meshwork Cells." *Invest Ophthalmol Vis Sci.* 52 (10): 7027-7037).

It has been shown that Bendavia is able to avert MPT by binding to cardiolipin within the inner mitochondria membrane. See, for example, Szeto et al., "The Mitochondrial-Targeted Compound SS-31 Re-energizes Ischemic Mitochondria by Interacting with Cardiolipin. 2013, 24, 1250-1261.

Furthermore, it has been shown, administration of Bendavia reduces reactive oxygen species (ROS) in the mitochondria, which is thought to lead to its ability to function in the treatment of mitochondria-associated diseases, disorders, or conditions. Bendavia has been (and/or is being) clinically evaluated, and has even proven to be clinically effective in certain contexts (See ClinicalTrials.gov Identifiers: NCT01754818, NCT01786915, NCT01518985, NCT01513200, NCT01755858, NCT01572909, NCT02245620, NCT01115920, NCT02388529, NCT02388464, NCT02367014, and NCT0243644), entering a Phase II Clinical Trial assessing skeleton muscle function of elderly patients. See clinical trial NCT02245620.

The success of Bendavia has led to the development of structural derivatives. The first attempts of designing Bendavia derivatives focused on maintaining the cationic and aromatic moieties thought to be essential for activity, while varying amino acid sequence. Particularly, hydrophobicity through, e.g., incorporation of a phenylalanine residue or derivative was thought to be of particular importance for biological activity. While investigating structure-activity relationships, both D- and L- amino acids were incorporated into sequence-variants; however, these studies focused on simple amino acid substitutions as opposed to investigating the 3-dimensional arrangement of the peptide resulting from its chiral configuration. This has led to Bendavia derivatives that have failed to provide further improvements relative to Bendavia. See, for example, WO 2011091357A1, WO2011/139992A1, WO2012/174117A1, WO2012/129427A1, WO2013/049697A1, WO2013/086020A1, WO2013/155334A1, WO2013/059071A1, WO2013/126775A1, WO2014/088631A1, WO2014/165607A1, WO2015/060462A1, WO2015/100376A1, and WO2015/134096A1, the entirety of which are incorporated herein by reference.

Provided Peptide Agents

Figure 2:
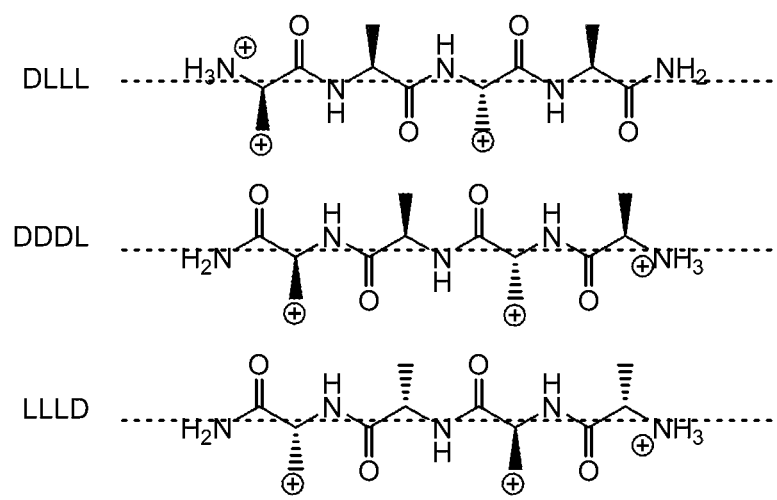
FIG. 2. Spatial configuration of peptide agents as described herein.

Among other things, the present disclosure encompasses insights relating to structural features characteristic of peptide agents that interact with cardiolipin. For example, among other things, the present disclosure encompasses the insight that the spatial configuration of the amino acid side chains, particularly configurations where each cationic moiety is present on the same side of the peptide, opposite from the remaining moieties (e.g., hydrophobic moieties, polar moieties, hydrophilic moieties), is more important than the actual amino acid sequences. See FIG. 1. Additionally, the present disclosure provides the insight that peptide agents effective in binding cardiolipin must maintain this spatial configuration, and allow for variations in chirality and amino acid sequence. For example, peptide chirality includes, for example, LDDD, DLDD, DDDL, LLLD, DDLL, LLDD, LLDL, DDLD, LDDL, DLLD, LDLD, DLDL, DDDD, or LLLL. By way of further example, the present disclosure provides the insight that reversing the amino acid order and inverting chirality (i.e., DDDL) leads to a peptide with a similar orientation to the DLLL orientation of Bendavia with a one bond shift, whereas reversing amino acid order and reversing chirality (i.e., LLLD) leads to inverted chiral orientation. See FIG. 2.

Without wishing to be bound by theory, it is believed that peptide agents of varying chirality that maintain configuration of the cationic groups spatially configured in the same direction, i.e., up or down, (e.g., DDDL, LLLD) may provide peptides agents at least as effective as Bendavia in the treatment of mitochondria-associated diseases, disorders, or conditions.

The present disclosure also identifies the source of a problem associated with prior work to identify desirable peptide agents that interact with cardiolipin. For example, among other things, the present disclosure demonstrates that peptide agents that bind cardiolipin do not necessarily require aromatic (i.e., hydrophobic) moieties. In some embodiments, the peptides of the present disclosure may comprise one or more hydrophilic or polar moieties. In some embodiments, the peptides of the present disclosure may comprise one or more hydrophilic or polar moieties spatially arranged opposite of the cationic moieties (e.g., cationic moieties up, hydrophilic/polar moieties down).

Among other things, the present disclosure encompasses insights relating to the effects of peptide agents on mitochondria function. The mitochondrial electron transport chain (ETC) plays a central role in energy generation in the cell. Mitochondrial dysfunctions diminish adenosine triphosphate (ATP) production and result in insufficient energy to maintain cell function. As energy output declines, the most energetic tissues are preferentially affected. To satisfy cellular energy demands, the mitochondrial ETC needs to be able to elevate its capacity to produce ATP at times of increased metabolic demand or decreased fuel supply. This mitochondrial plasticity is reduced in many diseases, disorders, or conditions. Bendavia, and other related therapeutics, were developed to improve mitochondrial function, wherein said improved mitochondrial function may provide protection from diseases, disorders, or conditions. Some or all of Bendavia's beneficial activities have sometimes been attributed to its ability to lower levels of reactive oxygen species ("ROS"), which in turn has been said to likely involve reduced ROS generation rather than traditional ROS scavenging (see, for example, Brown et al. *J. Cardiovasc. Pharmacol Thep.* 19:121, January 2014). The present disclosure encompasses peptides that improve mitochondria function as described above. In some embodiments, the peptides described herein improve mitochondria function beyond reducing ROS already present in the mitochondria. For example, peptide agents may increase mitochondria reserve capacity, which may provide increased resistance to MPT and mitochondria dysfunction, averting disease models that function through production of mitochondrial ROS. In some embodiments, the present peptide agents may act as cytoprotective and prevent ROS production in otherwise healthy cells.

In some embodiments, the present disclosure provides peptide agents of the following structure:

$$X^1-X^2-X^3-X^4 \qquad \qquad I$$

wherein:
$X^1$ is the N-terminal amino acid and $X^4$ is the C-terminal amino acid;
and further wherein:
$X^1$ comprises an N-terminal moiety selected from $-N(R)_2$ or $-N(R)-C(O)-R$;
$X^4$ comprises a C-terminal moiety selected from $-C(O)OR$ or $-C(O)N(R)_2$;
each R is independently hydrogen or optionally substituted $C_{1-6}$ aliphatic;
and further wherein:
either:
$X^2$ and $X^4$ are cationic amino acids; or
$X^1$ and $X^3$ are cationic amino acids,
and further wherein: $X^1$ is an L-amino acid, and each of $X^2$, $X^4$, and $X^4$ is a D-amino acid;
$X^2$ is an L-amino acid, and each of $X^1$, $X^3$, and $X^4$ is a D-amino acid;
$X^4$ is a D-amino acid, and each of $X^1$, $X^2$, and $X^3$ is an L-amino acid;
each of $X^1$, $X^2$, and $X^3$ is a D-amino acid, and $X^4$ is an L-amino acid;
each of $X^1$ and $X^2$ is a D-amino acid, and each of $X^3$ and $X^4$ is an L-amino acid;
each of $X^1$ and $X^2$ is an L-amino acid, and each of $X^3$ and $X^4$ is a D-amino acid;
$X^3$ is a D-amino acid, and each of $X^1$, $X^2$, and $X^4$ is an L-amino acid;

$X^3$ is a L-amino acid, and each of $X^1$, $X^2$, and $X^4$ is a D-amino acid;
each of $X^1$ and $X^4$ is an L-amino acid, and each of $X^2$ and $X^3$ is a D-amino acid;
each of $X^1$ and $X^4$ is an D-amino acid, and each of $X^2$ and $X^3$ is an L-amino acid;
each of $X^1$ and $X^3$ is an L-amino acid, and each of $X^2$ and $X^4$ is a D-amino acid;
each of $X^1$ and $X^3$ is an D-amino acid, and each of $X^2$ and $X^4$ is an L-amino acid;
each of $X^1$, $X^2$, $X^3$, and $X^4$ is a D-amino acid; or
each of $X^1$, $X^2$, $X^3$, and $X^4$ is an L-amino acid.

In some embodiments, a $X^1$ comprises an N-terminal moiety selected from $-N(R)_2$ or $-N(R)-C(O)-R$. In some embodiments, $X^1$ comprises an N-terminal moiety $-N(R)_2$. In some embodiments, $X^1$ comprises an N-terminal moiety $-NH_2$. In some embodiments, $X^1$ comprises an N-terminal moiety $-N(R)_3^+$. In some embodiments, $X^1$ comprises an N-terminal moiety $-NH_3^+$. In some embodiments, $X^1$ comprises an N-terminal moiety $-N(R)-C(O)-R$. In some embodiments, $X^1$ comprises an N-terminal moiety $-NH-C(O)-CH_3$.

In some embodiments, $X^4$ comprises a C-terminal moiety selected from $-C(O)OR$ or $-C(O)N(R)_2$. In some embodiments, $X^4$ comprises a C-terminal moiety $-C(O)OR$. In some embodiments, $X^4$ comprises a C-terminal moiety $-C(O)OH$. In some embodiments, $X^4$ comprises a C-terminal moiety $-C(O)N(R)_2$. In some embodiments, $X^4$ comprises a C-terminal moiety $-C(O)NH_2$.

In some embodiments, R is hydrogen. In some embodiments, R is $C_{1-6}$ aliphatic. In some embodiments, R is $C_{1-3}$ aliphatic. In some embodiments, R is $C_{4-6}$ aliphatic. In some embodiments, R is methyl. In some embodiments R is ethyl. In some embodiments, R is propyl.

In some embodiments, $X^1$ is an L-amino acid, and each of $X^2$, $X^4$, and $X^4$ is a D-amino acid; $X^2$ is an L-amino acid, and each of $X^1$, $X^3$, and $X^4$ is a D-amino acid; $X^4$ is a D-amino acid, and each of $X^1$, $X^2$, and $X^3$ is an L-amino acid; each of $X^1$, $X^2$, and $X^3$ is a D-amino acid, and $X^4$ is an L-amino acid; each of $X^1$ and $X^2$ is a D-amino acid, and each of $X^3$ and $X^4$ is an L-amino acid; each of $X^1$ and $X^2$ is an L-amino acid, and each of $X^3$ and $X^4$ is a D-amino acid; $X^3$ is a D-amino acid, and each of $X^1$, $X^2$, and $X^4$ is an L-amino acid; $X^3$ is a L-amino acid, and each of $X^1$ $X^2$, and $X^4$ is a D-amino acid; each of $X^1$ and $X^4$ is an L-amino acid, and each of $X^2$ and $X^3$ is a D-amino acid; each of $X^1$ and $X^4$ is an D-amino acid, and each of $X^2$ and $X^3$ is an L-amino acid; each of $X^1$ and $X^3$ is an L-amino acid, and each of $X^2$ and $X^4$ is a D-amino acid; each of $X^1$ and $X^3$ is an D-amino acid, and each of $X^2$ and $X^4$ is an L-amino acid; or each of $X^1$, $X^2$, $X^3$, and $X^4$ are D-amino acids.

In some embodiments, $X^1$ is an L-amino acid, and each of $X^2$, $X^4$, and $X^4$ is a D-amino acid. In some embodiments, $X^2$ is an L-amino acid, and each of $X^1$, $X^3$, and $X^4$ is a D-amino acid. In some embodiments, each of $X^1$ and $X^2$ is a D-amino acid, and each of $X^3$ and $X^4$ is an L-amino acid. In some embodiments, each of $X^1$ and $X^2$ is an L-amino acid, and each of $X^3$ and $X^4$ is a D-amino acid. In some embodiments, $X^3$ is a D-amino acid, and each of $X^1$, $X^2$, and $X^4$ is an L-amino acid. In some embodiments, $X^3$ is a L-amino acid, and each of $X^1$, $X^2$, and $X^4$ is a D-amino acid. In some embodiments, each of $X^1$ and $X^4$ is an L-amino acid, and each of $X^2$ and $X^3$ is a D-amino acid. In some embodiments, each of $X^1$ and $X^4$ is an D-amino acid, and each of $X^2$ and $X^3$ is an L-amino acid. In some embodiments, each of $X^1$ and $X^3$ is an L-amino acid, and each of $X^2$ and $X^4$ is a D-amino acid. In some embodiments, each of $X^1$ and $X^3$ is an D-amino acid, and each of $X^2$ and $X^4$ is an L-amino acid. In some embodiments, $X^4$ is a D amino acid, and each of $X^1$, $X^2$, and $X^3$ is an L amino acid. In some embodiments, $X^1$, $X^2$, and $X^3$ are D-amino acids, and $X^4$ is an L-amino acid. In some embodiments, each of $X^1$, $X^2$, $X^3$, and $X^4$ are D-amino acids. In some embodiments, each of $X^1$, $X^2$, $X^3$, and $X^4$ are L-amino acids.

In some embodiments, $X^2$ and $X^4$ are cationic amino acids. In some embodiments, $X^1$ and $X^3$ are cationic amino acids.

In some embodiments, $X^1$ and $X^3$ are hydrophobic amino acids and $X^2$ and $X^4$ are cationic amino acids. In some embodiments, $X^1$ and $X^3$ are cationic amino and $X^2$ and $X^4$ are hydrophobic amino acids. In some embodiments, $X^1$ and $X^3$ are hydrophilic amino acids and $X^2$ and $X^4$ are cationic amino acids. In some embodiments, $X^1$ and $X^3$ are cationic amino and $X^2$ and $X^4$ are hydrophilic amino acids.

In some embodiments, a cationic amino acid is selected from an amino acid comprising a cationic moiety. In some embodiments, a cationic amino acid is Dap. In some embodiments, a cationic amino acid is Dab. In some embodiments, each cationic amino acid is independently selected from Arg, Lys, or Orn. In some embodiments, each cationic amino acid is independently selected from L-Arg, D-Arg, L-Lys, D-Lys, L-Orn, or D-Orn. In some embodiments, each cationic amino acid is independently selected from L-Arg or D-Arg. In some embodiments, each cationic amino acid is independently selected from L-Lys or D-Lys. In some embodiments, each cationic amino acid is independently selected from L-Orn or D-Orn.

In some embodiments, one cationic amino acid is L-Lys and another cationic amino acid is D-Arg. In some embodiments, one cationic amino acid is L-Orn, and another cationic amino acid is D-Arg. In some embodiments, one cationic amino acid is L-Orn, and another cationic amino acid is D-Orn. In some embodiments, one cationic amino acid is D-Orn, and another cationic amino acid is L-Arg. In some embodiments, one cationic amino acid is D-Lys, and another cationic amino acid is L-Arg. In some embodiments, each cationic amino acid is L-Orn or D-Orn.

In some embodiments, a cationic amino acid is L-Arg. In some embodiments, a cationic amino acid is D-Arg. In some embodiments, a cationic amino acid is L-Lys. In some embodiments, a cationic amino acid is D-Lys. In some embodiments, a cationic amino acid is L-Orn. In some embodiments, a cationic amino acid is D-Orn.

In some embodiments, a hydrophobic amino acid is selected from an amino acid comprising a hydrophobic moiety. In some embodiments, each hydrophobic amino acid is independently selected from Leu or Phe. In some embodiments, each hydrophobic amino acid is independently selected from L-Leu, D-Leu, or L-Phe, D-Phe. In some embodiments, each hydrophobic amino acid is independently selected from L-Leu or D-Leu. In some embodiments, each hydrophobic amino acid is independently selected from L-Phe or D-Phe.

In some embodiments, a hydrophobic amino acid is L-Leu. In some embodiments, a hydrophobic amino acid is D-Leu. In some embodiments, a hydrophobic amino acid is L-Phe. In some embodiments, a hydrophobic amino acid is D-Phe.

In some embodiments, a hydrophilic amino acid is L-Tyr. In some embodiments, a hydrophilic amino acid is D-Tyr. In some embodiments, a hydrophilic amino acid is L-Dmt. In some embodiments, a hydrophilic amino acid is D-Dmt. In some embodiments, each hydrophilic amino acid is independently selected from L-Dmt, D-Dmt, L-Tyr, or D-Tyr. In some embodiments, each hydrophilic amino acid is independently selected from L-Dmt or D-Dmt. In some embodiments, each hydrophilic amino acid is independently selected from L-Tyr or D-Tyr.

In some embodiments, a polar amino acid is L-Tyr. In some embodiments, a polar amino acid is D-Tyr. In some embodiments, a polar amino acid is L-Dmt. In some embodiments, a polar amino acid is D-Dmt. In some embodiments, each polar amino acid is independently selected from L-Dmt, D-Dmt, L-Tyr, or D-Tyr. In some embodiments, each polar amino acid is independently selected from L-Dmt or D-Dmt. In some embodiments, each polar amino acid is independently selected from L-Tyr or D-Tyr.

In some embodiments, $X^1$ is selected from standard amino acids. In some embodiments, $X^1$ is selected from nonstandard amino acids.

In some embodiments, $X^1$ is a cationic amino acid. In some embodiments, $X^1$ is an anionic amino acid. In some embodiments, $X^1$ is a hydrophilic amino acid. In some embodiments, $X^1$ is a polar amino acid. In some embodiments, $X^1$ is a hydrophobic amino acid.

In some embodiments, $X^1$ is L-Phe. In some embodiments, $X^1$ is D-Phe. In some embodiments, $X^1$ is L-Leu. In some embodiments, $X^1$ is D-Leu. In some embodiments, $X^1$ is D-Dmt. In some embodiments, $X^1$ is L-Dmt. In some embodiments, $X^1$ is D-Tyr. In some embodiments, $X^1$ is L-Tyr.

In some embodiments, $X^2$ is selected from standard amino acids. In some embodiments, $X^2$ is selected from nonstandard amino acids.

In some embodiments, $X^2$ is a cationic amino acid. In some embodiments, $X^2$ is a hydrophobic amino acid. In some embodiments, $X^2$ is an anionic amino acid. In some embodiments, $X^2$ is a hydrophilic amino acid. In some embodiments, $X^2$ is a polar amino acid.

In some embodiments, $X^2$ is L-Lys. In some embodiments, $X^2$ is L-Orn. In some embodiments, $X^2$ is D-Orn. In some embodiments, $X^2$ is D-Lys. In some embodiments, $X^2$ is L-Arg. In some embodiments, $X^2$ is D-Arg.

In some embodiments, $X^3$ is selected from standard amino acids. In some embodiments, $X^3$ is selected from nonstandard amino acids.

In some embodiments, $X^3$ is a hydrophobic amino acid. In some embodiments, $X^3$ is a cationic amino acid. In some embodiments, $X^3$ is an anionic amino acid. In some embodiments, $X^3$ is a hydrophilic amino acid. In some embodiments, $X^3$ is a polar amino acid.

In some embodiments, $X^3$ is L-Dmt. In some embodiments, $X^3$ is L-Tyr. In some embodiments, $X^3$ is D-Tyr. In some embodiments, $X^3$ is D-Dmt. In some embodiments, $X^3$ is L-Leu. In some embodiments, $X^3$ is L-Phe. In some embodiments, $X^3$ is D-Leu. In some embodiments, $X^3$ is D-Phe.

In some embodiments, $X^4$ is selected from standard amino acids. In some embodiments, $X^4$ is selected from nonstandard amino acids.

In some embodiments, $X^4$ is a cationic amino acid. In some embodiments, $X^4$ is a hydrophobic amino acid. In some embodiments, $X^4$ is an anionic amino acid. In some embodiments, $X^4$ is a hydrophilic amino acid. In some embodiments, $X^4$ is a polar amino acid.

In some embodiments, $X^4$ is D-Arg. In some embodiments, $X^4$ is D-Orn. In some embodiments, $X^4$ is L-Arg. In some embodiments, $X^4$ is L-Orn. In some embodiments, $X^4$ is D-Lys. In some embodiments, $X^4$ is L-Lys.

In some embodiments, $X^1$ is D-Lys, $X^2$ is L-Phe, $X^3$ is D-Arg, and $X^4$ is D-Phe. In some embodiments, $X^1$ is D-Lys, $X^2$ is D-Phe, $X^3$ is L-Arg, and $X^4$ is D-Phe. In some embodiments, $X^1$ is L-Orn, $X^2$ is D-Tyr, $X^3$ is D-Orn, and $X^4$ is D-Phe.

In some embodiments, $X^1$ is L-Phe, $X^2$ is D-Orn, $X^3$ is D-Tyr, and $X^4$ is D-Orn. In some embodiments, $X^1$ is L-Orn, $X^2$ is D-Tyr, $X^3$ is D-Orn, and $X^4$ is D-Phe. In some embodiments, $X^1$ is D-Phe, $X^2$ is L-Orn, $X^3$ is D-Tyr, and $X^4$ is D-Orn. In some embodiments, $X^1$ is D-Orn, $X^2$ is L-Tyr, $X^3$ is D-Orn, and $X^4$ is D-Phe. In some embodiments, $X^1$ is D-Phe, $X^2$ is D-Orn, $X^3$ is D-Tyr, and $X^4$ is L-Orn. In some embodiments, $X^1$ is D-Orn, $X^2$ is D-Tyr, $X^3$ is D-Orn, and $X^4$ is L-Phe. In some embodiments, $X^1$ is L-Phe, $X^2$ is L-Orn, $X^3$ is L-Tyr, and $X^4$ is D-Orn. In some embodiments, $X^1$ is L-Orn, $X^2$ is L-Tyr, $X^3$ is L-Orn, and $X^4$ is D-Phe. In some embodiments, $X^1$ is D-Phe, $X^2$ is D-Orn, $X^3$ is L-Tyr, and $X^4$ is L-Orn. In some embodiments, $X^1$ is D-Orn, $X^2$ is D-Tyr, $X^3$ is L-Orn, and $X^4$ is L-Phe. In some embodiments, $X^1$ is L-Phe, $X^2$ is L-Orn, $X^3$ is D-Tyr, and $X^4$ is D-Orn. In some embodiments, $X^1$ is L-Orn, $X^2$ is L-Tyr, $X^3$ is D-Orn, and $X^4$ is D-Phe. In some embodiments, $X^1$ is L-Phe, $X^2$ is L-Orn, $X^3$ is D-Tyr, and $X^4$ is L-Orn. In some embodiments, $X^1$ is L-Orn, $X^2$ is L-Tyr, $X^3$ is D-Orn, and $X^4$ is L-Phe. In some embodiments, $X^1$ is D-Phe, $X^2$ is D-Orn, $X^3$ is L-Tyr, and $X^4$ is D-Orn. In some embodiments, $X^1$ is D-Orn, $X^2$ is D-Tyr, $X^3$ is L-Orn, and $X^4$ is D-Phe. In some embodiments, $X^1$ is L-Phe, $X^2$ is D-Orn, $X^3$ is D-Tyr, and $X^4$ is L-Orn. In some embodiments, $X^1$ is L-Orn, $X^2$ is D-Tyr, $X^3$ is D-Orn, and $X^4$ is L-Phe. In some embodiments, $X^1$ is D-Phe, $X^2$ is L-Orn, $X^3$ is L-Tyr, and $X^4$ is D-Orn. In some embodiments, $X^1$ is D-Orn, $X^2$ is L-Tyr, $X^3$ is L-Orn, and $X^4$ is D-Phe. In some embodiments, $X^1$ is L-Phe, $X^2$ is D-Orn, $X^3$ is L-Tyr, and $X^4$ is D-Orn. In some embodiments, $X^1$ is L-Orn, $X^2$ is D-Tyr, $X^3$ is L-Orn, and $X^4$ is D-Phe. In some embodiments, $X^1$ is D-Phe, $X^2$ is L-Orn, $X^3$ is D-Tyr, and $X^4$ is L-Orn. In some embodiments, $X^1$ is D-Orn, $X^2$ is L-Tyr, $X^3$ is D-Orn, and $X^4$ is L-Phe. In some embodiments, $X^1$ is D-Phe, $X^2$ is D-Orn, $X^3$ is D-Tyr, and $X^4$ is D-Orn. In some embodiments, $X^1$ is D-Orn, $X^2$ is D-Tyr, $X^3$ is D-Orn, and $X^4$ is D-Phe. In some embodiments, $X^1$ is L-Orn, $X^2$ is L-Orn, $X^3$ is L-Tyr, and $X^4$ is L-Orn. In some embodiments, $X^1$ is L-Orn, $X^2$ is L-Tyr, $X^3$ is L-Orn, and $X^4$ is L-Phe.

In some embodiments, the present disclosure provides peptide agents selected from those in Table 1.

TABLE 1

| Peptide Number | Peptide Sequence |
| --- | --- |
| I-11 | (L-Phe)(L-Lys)(L-Dmt)(D-Arg)-NH$_2$ |
| I-12 | (L-Phe)(L-Orn)(L-Dmt)(D-Arg)-NH$_2$ |
| I-13 | (L-Phe)(L-Orn)(L-Dmt)(D-Orn)-NH$_2$ |
| I-14 | (L-Phe)(L-Orn)(L-Tyr)(D-Arg)-NH$_2$ |
| I-15 | (L-Phe)(L-Orn)(L-Tyr)(D-Orn)-NH$_2$ |
| I-16 | (D-Phe)(D-Orn)(D-Tyr)(L-Arg)-NH$_2$ |
| I-17 | (D-Phe)(D-Orn)(D-Tyr)(L-Orn)-NH$_2$ |
| I-18 | (D-Phe)(D-Lys)(D-Dmt)(L-Arg)-NH$_2$ |
| I-19 | (D-Phe)(D-Orn)(D-Dmt)(L-Arg)-NH$_2$ |
| I-20 | (D-Phe)(D-Orn)(D-Dmt)(L-Orn)-NH$_2$ |

TABLE 1-continued

| Peptide Number | Peptide Sequence |
| --- | --- |
| I-28 | (L-Phe)(L-Lys)(L-Leu)(D-Arg)-NH$_2$ |
| I-29 | (L-Phe)(L-Lys)(L-Phe)(D-Arg)-NH$_2$ |
| I-30 | (L-Phe)(L-Orn)(L-Leu)(D-Arg)-NH$_2$ |
| I-31 | (L-Phe)(L-Orn)(L-Leu)(D-Orn)-NH$_2$ |
| I-32 | (L-Leu)(L-Orn)(L-Leu)(D-Orn)-NH$_2$ |
| I-33 | (L-Phe)(L-Orn)(L-Phe)(D-Orn)-NH$_2$ |
| I-34 | (D-Phe)(D-Lys)(D-Leu)(L-Arg)-NH$_2$ |
| I-35 | (D-Phe)(D-Orn)(D-Leu)(L-Arg)-NH$_2$ |
| I-36 | (D-Phe)(D-Orn)(D-Leu)(L-Orn)-NH$_2$ |
| I-37 | (D-Leu)(D-Orn)(D-Leu)(L-Orn)-NH$_2$ |
| I-38 | (D-Phe)(D-Orn)(D-Phe)(L-Orn)-NH$_2$ |
| I-39 | (D-Phe)(D-Orn)(D-Tyr)(D-Orn)-NH$_2$ |

In some embodiments, a peptide has an amino acid sequence as set forth above in Table 1. In some embodiments, such a peptide may have a C-terminal free amide (i.e., as indicated in Table 1); alternatively, in some embodiments, such a peptide may have a C-terminus that is a free acid rather than an amide. In such instances, presence of a free acid may be indicated in the peptide number using an asterisk (*). For instance, where I-11 indicates (L-Phe)(L-Lys)(L-Dmt)(D-Arg)-NH$_2$, depicted above, I-11* indicates (L-Phe)(L-Lys)(L-Dmt)(D-Arg)-OH. In some embodiments, a peptide having an amino acid sequence as set forth above in Table 1 has an N-terminus that is acetylated. In such instances, acetylation of the N-terminus may be indicated in the peptide number by including the superscript "NTA" (i.e., N-terminus acetylated). For instance, the N-terminus acetylated version of I-11 may be indicated as I-11$^{NTA}$. In instances wherein the C-terminus is a free acid rather than an amide and wherein the N-terminus is acetylated, both indicators may be used in the peptide number, e.g., I-11$^{NTA/*}$. The present invention contemplates the C-terminus free acid form, N-terminus acetylated form, and combinations thereof, of each peptide sequence depicted in Table 1, above.

In some embodiments, the provided peptide agents are of formula II:

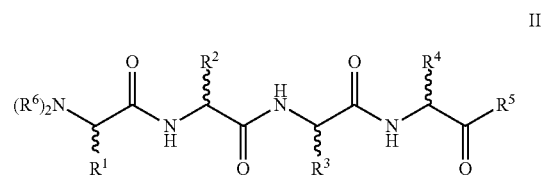

wherein:
each of $R^1$, $R^2$, $R^3$, and $R^4$ is independently —H or an optionally substituted group selected from the group consisting of $C_{1-20}$ aliphatic; —(CH$_2$)$_m$—N(R)$_2$; —(CH$_2$)$_n$—NR—CH—(NR$_2$)$_2$; phenyl substituted with 0-5 occurrences of —R or —OR; and -Cy;

each R is independently hydrogen or optionally substituted $C_{1-6}$ aliphatic;
m is 0-12;
n is 0-6;
each -Cy is independently an optionally substituted ring selected from the group consisting of a 3-9 membered saturated or partially unsaturated monocyclic carbocyclic ring; a 3-9 membered saturated or partially unsaturated monocyclic heterocyclic ring having 1-3 heteroatoms independently selected from nitrogen, oxygen, or sulfur; and a 5-6 membered heteroaryl ring having 1-3 heteroatoms independently selected from nitrogen, oxygen, or sulfur;
$R^5$ is —OR or —N(R)$_2$; and
each $R^6$ is independently —R or —C(O)R;
wherein $R^1$, $R^2$, $R^3$, and $R^4$ alternate between comprising a cationic moiety.

In some embodiments, $R^1$, $R^2$, $R^3$, and $R^4$ alternate between comprising a cationic moiety or a hydrophobic moiety. In some embodiments $R^1$, $R^2$, $R^3$, and $R^4$ alternate from being derived from a cationic amino acid. In some embodiments $R^1$, $R^2$, $R^3$, and $R^4$ alternate from being derived from a cationic amino acid or a hydrophobic amino acid.

In some embodiments, $R^1$ and $R^3$ comprise a hydrophobic moiety. In some embodiments $R^1$ and $R^3$ comprise a cationic moiety. In some embodiments, $R^2$ and $R^4$ comprise a hydrophobic moiety. In some embodiments, $R^2$ and $R^4$ comprise a cationic moiety. In some embodiments, $R^1$ and $R^3$ comprise a hydrophobic moiety, and $R^2$ and $R^4$ comprise a cationic moiety. In some embodiments, $R^1$ and $R^3$ comprise a cationic moiety, and $R^2$ and $R^4$ comprise a hydrophobic moiety.

In some embodiments, $R^1$ is hydrogen. In some embodiments, $R^1$ is an optionally substituted group selected from the group consisting of $C_{1-20}$ aliphatic; —(CH$_2$)$_m$—N(R)$_2$; —(CH$_2$)$_n$—NR—CH—(NR$_2$)$_2$; phenyl substituted with 0-5 occurrences of R or OR; and Cy. In some embodiments, $R^1$ is optionally substituted $C_{1-20}$ aliphatic. In some embodiments, $R^1$ is optionally substituted $C_{1-10}$ aliphatic. In some embodiments, $R^1$ is optionally substituted $C_{1-6}$ aliphatic. In some embodiments, $R^1$ is optionally substituted $C_{1-4}$ aliphatic. In some embodiments, $R^1$ is optionally substituted $C_{1-3}$ aliphatic. In some embodiments, $R^1$ is $C_{1-20}$ aliphatic. In some embodiments, $R^1$ is $C_{1-10}$ aliphatic. In some embodiments, $R^1$ is $C_{1-6}$ aliphatic. In some embodiments, $R^1$ is $C_{1-4}$ aliphatic. In some embodiments, $R^1$ is $C_{1-3}$ aliphatic. In some embodiments, $R^1$ is isopropyl. In some embodiments, $R^1$ is butyl. In some embodiments, $R^1$ is s-butyl. In some embodiments, $R^1$ is isobutyl. In some embodiments, $R^1$ is optionally substituted phenyl substituted with 0-5 occurrences of —R or —OR. In some embodiments, $R^1$ is optionally substituted phenyl. In some embodiments, $R^1$ is phenyl.

In some embodiments, $R^2$ is hydrogen. In some embodiments, $R^2$ is an optionally substituted group selected from the group consisting of $C_{1-20}$ aliphatic; —(CH$_2$)$_m$—N(R)$_2$; —(CH$_2$)$_n$—NR—CH—(NR$_2$)$_2$; phenyl substituted with 0-5 occurrences of —R or —OR; and Cy. In some embodiments, $R^2$ is optionally substituted —(CH$_2$)$_n$—N(R)$_2$. In some embodiments, $R^2$ is —(CH$_2$)$_m$—N(R)$_2$. In some embodiments, $R^2$ is —(CH$_2$)$_m$—N(R)$_2$, wherein m is 2. In some embodiments, $R^2$ is —(CH$_2$)$_m$—N(R)$_2$, wherein m is 3. In some embodiments, $R^2$ is —(CH$_2$)$_m$—N(R)$_2$, wherein m is 4. In some embodiments, $R^2$ is —(CH$_2$)$_m$—N(R)$_2$, wherein each —R is hydrogen. In some embodiments, $R^2$ is optionally substituted —(CH$_2$)$_n$—NR—CH—(NR$_2$)$_2$. In some embodiments, $R^2$ is —(CH$_2$)$_n$—NR—CH—(NR$_2$)$_2$. In some embodiments, $R^2$ is —(CH$_2$)$_n$—NR—CH—(NR$_2$)$_2$, wherein n is 2. In some embodiments, $R^2$ is —(CH$_2$)$_n$—NR—CH—(NR$_2$)$_2$, wherein n is 3. In some embodiments, $R^2$ is —(CH$_2$)$_n$—NR—CH—(NR$_2$)$_2$, wherein n is 4. In some embodiments, $R^2$ is —(CH$_2$)$_n$—NR—CH—(NR$_2$)$_2$, wherein —R is selected from methyl or hydrogen. In some embodiments, $R^2$ is —(CH$_2$)$_n$—NH—CH—(NH$_2$)$_2$. In some embodiments, $R^2$ is —(CH$_2$)$_n$—NH—CH—(NH$_2$)$_2$, wherein n is 3.

In some embodiments, $R^3$ is hydrogen. In some embodiments, $R^3$ is an optionally substituted group selected from the group consisting of $C_{1-20}$ aliphatic; —(CH$_2$)$_m$—N(R)$_2$; —(CH$_2$)$_n$—NR—CH—(NR$_2$)$_2$; phenyl substituted with 0-5 occurrences of —R or —OR; and -Cy. In some embodiments, $R^3$ is optionally substituted $C_{1-20}$ aliphatic. In some embodiments, $R^3$ is optionally substituted $C_{1-10}$ aliphatic. In some embodiments, $R^3$ is optionally substituted $C_{1-6}$ aliphatic. In some embodiments, $R^3$ is optionally substituted $C_{1-4}$ aliphatic. In some embodiments, $R^3$ is optionally substituted $C_{1-3}$ aliphatic. In some embodiments, $R^3$ is $C_{1-20}$ aliphatic. In some embodiments, $R^3$ is $C_{1-10}$ aliphatic. In some embodiments, $R^3$ is $C_{1-6}$ aliphatic. In some embodiments, $R^3$ is $C_{1-4}$ aliphatic. In some embodiments, $R^3$ is $C_{1-3}$ aliphatic. In some embodiments, $R^3$ is isopropyl. In some embodiments, $R^3$ is butyl. In some embodiments, $R^3$ is s-butyl. In some embodiments, $R^3$ is isobutyl. In some embodiments, $R^3$ is optionally substituted phenyl substituted with 0-5 occurrences of —R or —OR. In some embodiments, $R^3$ is optionally substituted phenyl. In some embodiments, $R^3$ is phenyl. In some embodiments, $R^3$ is phenyl substituted with 0-5 occurrences of —R or —OR. In some embodiments, $R^3$ is phenyl substituted with 0-4 occurrences of —R or —OR. In some embodiments, $R^3$ is phenyl substituted with 0-3 occurrences of —R or —OR. In some embodiments, $R^3$ is phenyl substituted with 0-2 occurrences of —R or —OR. In some embodiments, $R^3$ is phenyl substituted with 0-1 occurrences of —R or —OR. In some embodiments, $R^3$ is phenyl substituted with 1-5 occurrences of —R or —OR. In some embodiments, $R^3$ is phenyl substituted with 2-5 occurrences of —R or —OR. In some embodiments, $R^3$ is phenyl substituted with 3-5 occurrences of —R or —OR. In some embodiments, $R^3$ is phenyl substituted with 4-5 occurrences of —R or —OR. In some embodiments, $R^3$ is phenyl substituted with 1-4 occurrences of —R or —OR. In some embodiments, $R^3$ is phenyl substituted with 2-3 occurrences of —R or —OR. In some embodiments, $R^3$ is phenyl substituted with 1 occurrence of —R or —OR. In some embodiments, $R^3$ is phenyl substituted with —OR. In some embodiments, $R^3$ is phenyl substituted with —OH. In some embodiments, $R^3$ is phenyl substituted with 3 occurrences of —R or —OR. In some embodiments, $R^3$ is phenyl substituted with 2 occurrences of —R and 1 occurrence of —OR. In some embodiments, $R^3$ is phenyl substituted with 2 occurrences of —CH$_3$ and 1 occurrence of —OH.

In some embodiments, $R^4$ is hydrogen. In some embodiments, $R^4$ is an optionally substituted group selected from the group consisting of $C_{1-20}$ aliphatic; —(CH$_2$)$_m$—N(R)$_2$; —(CH$_2$)$_n$—NR—CH—(NR$_2$)$_2$; phenyl substituted with 0-5 occurrences of —R or —OR; and Cy. In some embodiments, $R^4$ is optionally substituted —(CH$_2$)$_m$—N(R)$_2$. In some embodiments, $R^4$ is —(CH$_2$)$_m$—N(R)$_2$. In some embodiments, $R^4$ is —(CH$_2$)$_m$—N(R)$_2$, wherein m is 2. In some embodiments, $R^4$ is —(CH$_2$)$_m$—N(R)$_2$, wherein m is 3. In some embodiments, $R^4$ is —(CH$_2$)$_m$—N(R)$_2$, wherein m is 4. In some embodiments, $R^4$ is —(CH$_2$)$_m$—N(R)$_2$, wherein each —R is hydrogen. In some embodiments, $R^4$ is optionally substituted —(CH$_2$)$_n$—NR—CH—(NR$_2$)$_2$. In some embodiments, R$^4$ is —(CH$_2$)$_n$—NR—CH—(NR$_2$)$_2$. In some embodiments, R$^4$ is —(CH$_2$)$_n$—NR—CH—(NR$_2$)$_2$, wherein n is 2. In some embodiments, R$^4$ is —(CH$_2$)$_n$—NR—CH—(NR$_2$)$_2$, wherein n is 3. In some embodiments, R$^4$ is —(CH$_2$)$_n$—NR—CH—(NR$_2$)$_2$, wherein n is 4. In some embodiments, R$^4$ is —(CH$_2$)$_n$—NR—CH—(NR$_2$)$_2$, wherein —R is selected from methyl or hydrogen. In some embodiments, R$^4$ is —(CH$_2$)$_n$—NH—CH—(NH$_2$)$_2$. In some embodiments, R$^4$ is —(CH$_2$)$_n$—NH—CH—(NH$_2$)$_2$, wherein n is 3.

In some embodiments, R$^5$ is —OR or —N(R)$_2$. In some embodiments, R$^5$ is —OR. In some embodiments, R$^5$ is —OH. In some embodiments, R$^5$ is —N(R)$_2$. In some embodiments, R$^5$ is —NH$_2$.

In some embodiments, each R$^6$ is independently —R or —C(O)R. In some embodiments, each R$^6$ is —R. In some embodiments, each R$^6$ is —H. In some embodiments, one occurrence of R$^6$ is —R, and another occurrence of R$^6$ is —C(O)R. In some embodiments, one occurrence of R$^6$ is —R, and another occurrence of R$^6$ is —C(O)CH$_3$.

In some embodiments, R is hydrogen. In some embodiments, R is optionally substituted C$_{1-6}$ aliphatic. In some embodiments, R is optionally substituted C$_{1-3}$ aliphatic. In some embodiments, R is optionally substituted C$_{4-6}$ aliphatic. In some embodiments, R is optionally substituted methyl. In some embodiments, R is optionally substituted ethyl. In some embodiments, R is optionally substituted propyl. In some embodiments, R is optionally substituted butyl. In some embodiments, R is optionally substituted pentyl. In some embodiments, R is optionally substituted hexyl. In some embodiments, R is methyl. In some embodiments, R is ethyl. In some embodiments, R is propyl. In some embodiments, R is butyl. In some embodiments, R is pentyl. In some embodiments, R is hexyl.

In some embodiments, m is 0-12. In some embodiments, m is 0-6. In some embodiments, m is 1-6. In some embodiments, m is 6-12. In some embodiments, m is 0-4. In some embodiments, m is 0-3. In some embodiments, m is 0-2. In some embodiments, m is 0-1. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12.

In some embodiments, n is 0-6. In some embodiments, n is 1-6. In some embodiments, n is 4-6. In some embodiments, n is 0-3. In some embodiments, n is 1-3. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, each -Cy is independently an optionally substituted ring selected from the group consisting of a 3-9 membered saturated or partially unsaturated monocyclic carbocyclic ring; a 3-9 membered saturated or partially unsaturated monocyclic heterocyclic ring having 1-3 heteroatoms independently selected from nitrogen, oxygen, or sulfur; and a 5-6 membered heteroaryl ring having 1-3 heteroatoms independently selected from nitrogen, oxygen, or sulfur. In some embodiments, -Cy is an optionally substituted 3-9 membered saturated or partially unsaturated monocyclic carbocyclic ring. In some embodiments, -Cy is an optionally substituted 3-9 membered saturated or partially unsaturated monocyclic heterocyclic ring having 1-3 heteroatoms independently selected from nitrogen, oxygen, or sulfur. In some embodiments, -Cy is an optionally substituted 5-6 membered heteroaryl ring having 1-3 heteroatoms independently selected from nitrogen, oxygen, or sulfur.

In some embodiments, the provided peptide agents are of formula III:

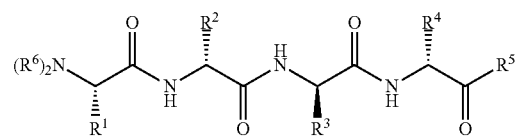

III wherein R$^1$, R$^2$, R$^3$, R$^4$, R, m, n, Cy, R$^5$, and R$^6$ are as defined above.

In some embodiments, the provided peptide agents are of formula IV:

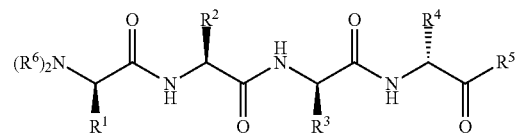

IV wherein R$^1$, R$^2$, R$^3$, R$^4$, R, m, n, Cy, R$^5$, and R$^6$ are as defined above.

In some embodiments, the provided peptide agents are of formula V:

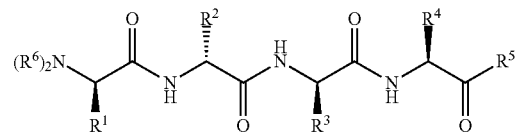

V wherein R$^1$, R$^2$, R$^3$, R$^4$, R, m, n, Cy, R$^5$, and R$^6$ are as defined above.

In some embodiments, the provided peptide agents are of formula VI:

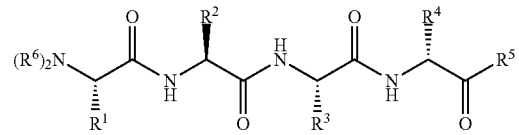

VI wherein R$^1$, R$^2$, R$^3$, R$^4$, R, m, n, Cy, R$^5$, and R$^6$ are as defined above.

In some embodiments, the provided peptide agents are of formula VII:

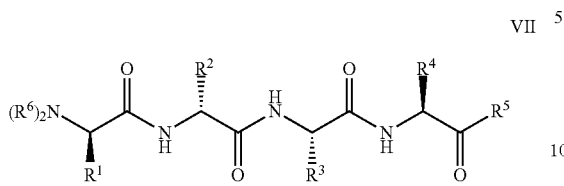

VII wherein $R^1$, $R^2$, $R^3$, $R^4$, R, m, n, Cy, $R^5$, and $R^6$ are as defined above.

In some embodiments, the provided peptide agents are of formula VIII:

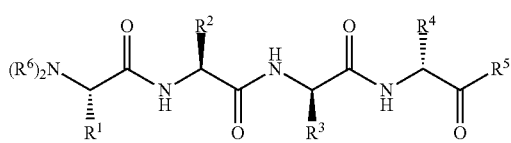

VIII wherein $R^1$, $R^2$, $R^3$, $R^4$, R, m, n, Cy, $R^5$, and $R^6$ are as defined above.

In some embodiments, the provided peptide agents are of formula IX:

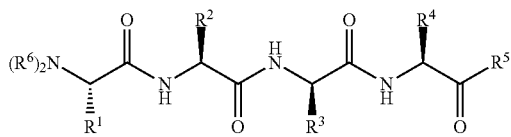

IX wherein $R^1$, $R^2$, $R^3$, $R^4$, R, m, n, Cy, $R^5$, and $R^6$ are as defined above.

In some embodiments, the provided peptide agents are of formula X:

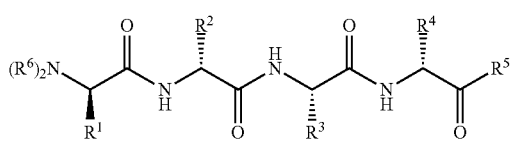

X wherein $R^1$, $R^2$, $R^3$, $R^4$, R, m, n, Cy, $R^5$, and $R^6$ are as defined above.

In some embodiments, the provided peptide agents are of formula XI:

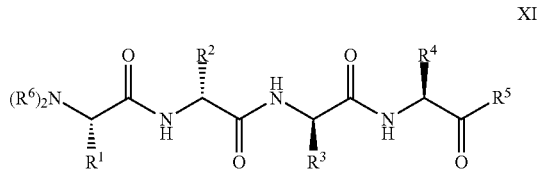

XI wherein $R^1$, $R^2$, $R^3$, $R^4$, R, m, n, Cy, $R^5$, and $R^6$ are as defined above.

In some embodiments, the provided peptide agents are of formula XII:

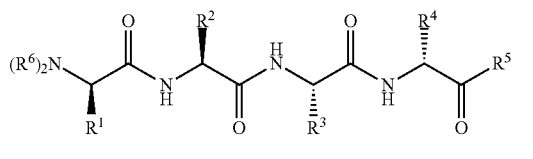

XII wherein $R^1$, $R^2$, $R^3$, $R^4$, R, m, n, Cy, $R^5$, and $R^6$ are as defined above.

In some embodiments, the provided peptide agents are of formula XIII:

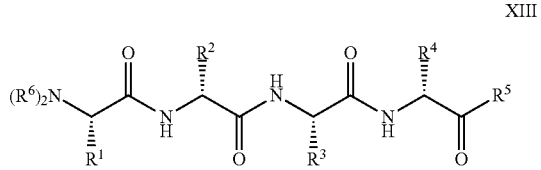

XIII wherein $R^1$, $R^2$, $R^3$, $R^4$, R, m, n, Cy, $R^5$, and $R^6$ are as defined above.

In some embodiments, the provided peptide agents are of formula XIV:

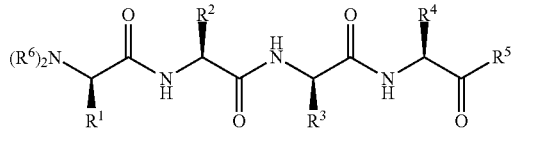

XIV wherein $R^1$, $R^2$, $R^3$, $R^4$, R, m, n, Cy, $R^5$, and $R^6$ are as defined above.

In some embodiments, the provided peptide agents are of formula XV:

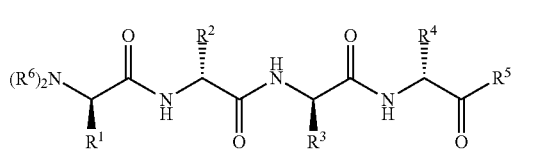

XV wherein $R^1$, $R^2$, $R^3$, $R^4$, R, m, n, Cy, $R^5$, and $R^6$ are as defined above.

In some embodiments, the provided peptide agents are of formula XVI:

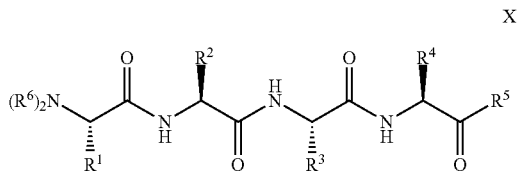

XVI wherein $R^1$, $R^2$, $R^3$, $R^4$, R, m, n, Cy, $R^5$, and $R^6$ are as defined above.

In some embodiments, a provided peptide agent is characterized in that, when contacted with a cell, modulates mitochondrial function in the cell. In some embodiments, a provided peptide agent is characterized in that, when contacted with a cell, it binds to an inner mitochondrial membrane. In some embodiments, provided peptide agents are characterized in that it binds to cardiolipin.

In some embodiments, provided peptides agents are characterized in that they improve mitochondrial activity. Defective mitochondrial activity, including but not limited to failure at any step of the elaborate multi-complex mitochondrial assembly, known as the electron transport chain (ETC), may result in (i) decreases in ATP production, (ii) increases in the generation of highly reactive free radicals (e.g., superoxide, peroxynitrite and hydroxyl radicals, and hydrogen peroxide), (iii) disturbances in intracellular calcium homeostasis and (iv) the release of factors (such as such as cytochrome c and "apoptosis inducing factor") that initiate or stimulate the apoptosis cascade. Because of these biochemical changes, mitochondrial dysfunction has the potential to cause widespread damage to cells and tissues.

Further without wishing to be bound by any particular theory, the present disclosure proposes that, in at least some embodiments, a provided peptide agent may target the inner mitochondrial membrane, for example, cardiolipin, to optimize efficiency of the electron transport chain (ETC) and thereby restore cellular bioenergetics associated with aging or a disease, disorder, or condition.

In some embodiments, provided peptide agents are characterized in that they increase mitochondrial reserve capacity, while the mitochondrial oxygen consumption rate remains relatively unchanged. For example, in some embodiments, provided peptide agents show increased mitochondrial reserve capacity, while the mitochondrial oxygen consumption rate remains relatively unchanged when tested for mitochondrial stress in XFe96 Seahorse Functional Mitochondrial Toxicity Assay.

In some embodiments, provided peptide agents are characterized in that, when tested in a Functional Mitochondrial Toxicity XFe96 Seahorse assay increases Reserve Capacity. In some embodiments, provided peptide agents are characterized in that, when tested in a Functional Mitochondrial Toxicity XFe96 Seahorse assay increases Reserve Capacity within an $AC_{50}$ range of about 0.1 µM to about 100 µM. In some embodiments, provided peptide agents are characterized in that, when tested in a Functional Mitochondrial Toxicity XFe96 Seahorse assay increases Reserve Capacity within an $AC_{50}$ range of about 0.5 µM to about 100 µM. In some embodiments, provided peptide agents are characterized in that, when tested in a Functional Mitochondrial Toxicity XFe96 Seahorse assay increases Reserve Capacity within an $AC_{50}$ range of about 0.5 µM to about 50 µM. In some embodiments, provided peptide agents are characterized in that, when tested in a Functional Mitochondrial Toxicity XFe96 Seahorse assay increases Reserve Capacity within an $AC_{50}$ range of about 0.5 µM to about 10 µM. In some embodiments, provided peptide agents are characterized in that, when tested in a Functional Mitochondrial Toxicity XFe96 Seahorse assay increases Reserve Capacity within an $AC_{50}$ range of about 0.5 µM to about 1 µM.

In some embodiments, provided peptide agents show one or more activities that is/are comparable to that of an appropriate reference agent. In some embodiments, an appropriate reference agent is or comprises a tetrapeptide agent of DLLL chirality. In some embodiments, an appropriate reference peptide agent is or comprises Bendavia. In some embodiments, an appropriate reference peptide agent is or comprises D-Arg-Dmt-Lys-Phe-$NH_2$. In some embodiments, provided peptides show an increased reserve capacity, while oxygen consumption rate remains relatively unchanged, that is comparable to that of Bendavia.

In some embodiments, provided peptide agents are characterized in that, when tested in a Functional Mitochondrial Toxicity XFe96 Seahorse assay, exhibits a Reserve Capacity $AC_{50}$ within an order of magnitude of that shown by Bendavia under comparable conditions. In some embodiments, provided peptide agents are characterized in that, when tested in a Functional Mitochondrial Toxicity XFe96 Seahorse assay, increases Reserve Capacity with an $AC_{50}$ within 2-fold of that shown by Bendavia under comparable conditions. In some embodiments, provided peptide agents are characterized in that, when tested in a Functional Mitochondrial Toxicity XFe96 Seahorse assay, increases Reserve Capacity with an $AC_{50}$ similar to or greater than that shown by Bendavia under comparable conditions.

In some embodiments, provided peptide agents show greater resistance to trypsin degradation as compared with an appropriate reference agent. In some embodiments, provided peptide agents show greater resistance to trypsin degradation as compared to Bendavia.

Uses

In some embodiments, the present disclosure provides a method of inhibiting mitochondrial respiration in a patient or in a biological sample, comprising a step of administering to said patient or contacting said biological sample with a peptide agent or composition disclosed herein.

In some embodiments, the present disclosure provides a method of treating a subject suffering from or susceptible to a disease, disorder, or condition, which method comprises a step of:

administering a peptide agent or composition disclosed herein to a subject in need thereof.

Various diseases, disorders, and/or conditions may be related to mitochondria-function. In some embodiments, the present disclosure provides methods comprising administering to a subject suffering from or susceptible to a disease, disorder, or condition a pharmaceutically effective amount of a provided compound or composition. In some embodiments, a disease, disorder, or condition is related to abnormal mitochondria function. In some embodiments, a disease, disorder, or condition is associated with MPT. In certain embodiments, provided peptide agents or compositions reduce the number of mitochondria undergoing, and/or preventing MPT. In some embodiments, a disease, disorder, or condition is associated with mitochondrial dysfunction. In some embodiments, a disease, disorder, or condition is associated with improved Mitochondrial Reserve Capacity. In some embodiments, a disease, disorder, or condition is associated with improved Mitochondrial Reserve Capacity, as determined by assays described herein.

In some embodiments, a disease, disorder, or condition is or comprises ischemia and/or reperfusion of a tissue or organ.

In some embodiments, a disease, disorder, or condition is a neurologic, disease, disorder, or condition. In some embodiments, a disease, disorder or condition is Huntington's disease. In some embodiments, a disease, disorder or condition is Parkinson's disease. In some embodiments, a disease, disorder or condition is Alzheimer's disease. In some embodiments, a disease, disorder, or condition is Amyotrophic Lateral Sclerosis (ALS, also known as Lou Gherig's disease). In some embodiments, a disease, disorder or condition is Rett's syndrome.

In some embodiments, a disease, disorder, or condition is insulin resistance. In some embodiments, a disease, disorder, or condition is a metabolic syndrome. In some embodiments, a disease, disorder, or condition is a burn injury. In some embodiments, a disease, disorder, or condition is heart disease. In some embodiments, a disease, disorder, or condition is cogentital heart disease. In some embodiments, a disease, disorder, or condition is abnormal heart valves of valvular heart disease. In some embodiments, a disease, disorder, or condition is heart failure. In some embodiments, a disease, disorder, or condition is heart failure, wherein heart failure results from hypertension; ischemic heart disease; exposure to a cardiotoxic compound; myocarditis; thyroid disease; viral infection; gingivitis; drug abuse; alcohol abuse; pericarditis; atherosclerosis; vascular disease; hypertrophic cardiomyopathy; acute myocardial infarction; left ventricular systolic dysfunction; coronary bypass surgery; starvation; an eating disorder; or a genetic defect. In some embodiments, a disease, disorder, or condition is diabetic complications, for example, diabetic retinopathy. In some embodiments, a disease, disorder, or condition is an ophthalmic condition. In some embodiments, an ophthalmic condition comprises choroidal neovascularization, retinal degeneration, and oxygen-induced retinopathy.

In some embodiments, a disease, disorder, or condition is associated with oxidative damage. In some embodiments, a disease, disorder, or condition is associated with lipid peroxidation. In some embodiments, a disease, disorder, or condition In some embodiments, a disease, disorder, or condition is atherosclerosis.

In some embodiments, a disease, disorder, or condition is an inflammatory disease, disorder, or condition. In some embodiments, a disease, disorder, or condition is arthritis. In some embodiments, a disease, disorder, or condition multiple sclerosis. In some embodiments, a disease, disorder, or condition is an inflammatory disease, disorder, or condition is derived from a virus. Examples of viruses include, but are not limited to, hepatitis, A, B, C, human immunodeficiency virus, influenza virus, and bovine diarrhea virus. In some embodiments, a disease, disorder, or condition is derived from a bacteria. Examples of bacteria include, but are not limited to, *Escherichia coli, Klebsiella pneumoniae, Proteus* species, *Pseudomonas aeruginosa, Serratia, Bacteroides,* pneumococci, and streptococci.

In some embodiments, a disease, disorder, or condition is an auto-immune disease; diabetes mellitus, including Type I and Type II; mitochondria associated diseases, including but not limited to congenital muscular dystrophy with mitochondrial structural abnormalities, fatal infantile myopathy with severe mtDNA depletion and benign "later-onset" myopathy with moderate reduction in mtDNA, MELAS (mitochondrial encephalopathy, lactic acidosis, and stroke) and MIDD (mitochondrial diabetes and deafness); MERFF (myoclonic epilepsy ragged red fiber syndrome); arthritis; NARP (Neuropathy; Ataxia; Retinitis Pigmentosa); MNGIE (Myopathy and external ophthalmoplegia; Neuropathy; Gastro-Intestinal; Encephalopathy), LHON (leber's; Hereditary; Optic; Neuropathy), Kearns-Sayre disease; Pearson's Syndrome; PEO (Progressive External Ophthalmoplegia); Wolfram syndrome DIDMOAD (Diabetes Insipidus, Diabetes Mellitus, Optic Atrophy, Deafness); Leigh's Syndrome; dystonia; schizophrenia; and hyperproliferative disorders, such as cancer, tumors and psoriasis.

In some embodiments, a disease, disorder, or condition is muscular dystrophy. In some embodiments, a disease, disorder, or condition is Duchenne's muscular dystrophy. In some embodiments, a disease, disorder, or condition is Becker's muscular dystrophy.

In some embodiments, a disease, disorder,r or condition is a mitochondrial associated disease. In some embodiments, a disease, disorder, or condition is related to POLG. In some embodiments, a disease, disorder, or condition is related to POLG mutation.

Compositions

In some embodiments, peptide agents as provided herein are prepared and/or utilized in compositions, such as pharmaceutical compositions. In some embodiments, a provided pharmaceutical composition comprises a therapeutically effective amount of a provided peptide agent, and at least one pharmaceutically acceptable inactive ingredient selected from pharmaceutically acceptable diluents, pharmaceutically acceptable excipients, and pharmaceutically acceptable carriers. In some embodiments, the pharmaceutical composition is formulated for intravenous injection, oral administration, buccal administration, inhalation, nasal administration, topical administration, ophthalmic administration or optic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising a provided peptide agent or peptide composition, in admixture with a pharmaceutically acceptable excipient.

In therapeutic and/or diagnostic applications, provided peptide agents can be formulated for a variety of modes of administration, including systemic and topical or localized administration. Techniques and formulations generally may be found in Remington, The Science and Practice of Pharmacy, (20th ed. 2000).

Provided compounds and compositions thereof are effective over a wide dosage range. For example, in the treatment of adult humans, dosages from about 0.01 to about 10000 mg, from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, provided agents may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate provided compounds or compositions into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

The compounds can be formulated readily using pharmaceutically acceptable carriers well known in the art into dosages suitable for oral administration. Such carriers enable provided compounds and compositions to be formulated as tablets, pills, capsules, liquids, gels, syrups, slurries, suspensions and the like, for oral ingestion by a subject (e.g., patient) to be treated.

For nasal or inhalation delivery, provided compounds or compositions may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In certain embodiments, provided compounds and compositions are delivered to the CNS. In certain embodiments, provided compounds and compositions are delivered to the cerebrospinal fluid. In certain embodiments, provided compounds and compositions are administered to the brain parenchyma. In certain embodiments, provided compounds and compositions are delivered to an animal/subject by intrathecal administration, or intracerebroventricular administration. Broad distribution of provided compounds and compositions, described herein, within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

In some embodiments, cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with provided compounds or compositions. For example, chemotherapeutic agents or other anti-proliferative agents may be combined with provided compounds or compositions to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Methods of Making

In general, peptide agents as described herein, may be prepared through use of any available technology. In some embodiments, peptide agents are described herein, are synthesized by available solution-phase synthetic methods. In some embodiments, peptide agents described herein, are synthesized by available solid-phase synthetic methods.

In some embodiments, provided peptide agents comprise an unmodified N-terminus. In some embodiments, provided peptide agents comprise a modified N-terminus. In some embodiments, provided peptide agents comprise an acetylated N-terminus.

In some embodiments, provided peptide agents comprise a C-terminal carboxylic acid. In some embodiments, provided peptide agents comprise a C-terminal amide.

Identification and/or Characterization of Useful Compositions and/or Compounds

The present disclosure exemplifies preparation and/or testing/characterization of a variety of particular peptide agents. Those skilled in the art, reading the present disclosure, will appreciate that certain other peptides may be prepared in accordance with the teachings of the present disclosure, and peptide agents of interest may be identified and/or characterized as described herein.

To give but a few examples, in some embodiments, peptide agents or compositions may be characterized in that it shows activity, for example, in an in vitro model of mitochondria (for example, XFe96 Seahorse Mitochondrial Toxicity Assay), a MDX mouse model (for example, MDX mouse C57BL/10ScSn-DMd$^{mdx}$/J for Duchenne's muscular dystrophy; see Charles River Labs stock no 001801) or a R6/2 mouse model (for example, R6/2 mouse B6CBA-Tg (HDexon1)62Gpb/1J for Huntington disease; see Charles River Labs stock no 002810), and/or of one or more mitochondria-associated diseases, disorders, or conditions.

In some embodiments, the present disclosure provides methods of identifying or characterizing a mitochondrial respiration modulating agent, the method comprising the steps of contacting an agent to be identified or characterized with a system that includes cardiolipin and permits detection of one or more features of mitochondrial respiration with the agent, which agent shares structural features with a tetrapeptide agent of formula I, as defined above, which structural features include:
at least one cationic moiety that makes contact with cardiolipin; and identifying or characterizing the agent as a mitochondrial respiration modulating agent if the one or more features of mitochondrial respiration in the system when the agent is present as compared with when it is absent.

In some embodiments, the agent is a peptide agent according to any embodiment as described herein.

EXEMPLIFICATION

Example 1

Peptide Synthesis

In some embodiments, peptide agents are synthesized according to standard solution phase peptide synthesis techniques; in some embodiments peptide agents are synthesized according to standard solid phase peptide synthesis techniques.

Example 2

Functional Mitochondrial Toxicity Assay (HepG2 Human Liver Cancer Cell Line) General Protocol The present Examples interrogate the two major energy producing pathways in the cell, mitochondrial respiration and glycolysis. HepG2 human liver cancer cell lines were dosed with test compounds and in real time the extracellular oxygen levels and pH were measured using the XFe96 flux analyser (Seahorse Biosciences). XFe Technology uses solid-state sensors to simultaneously measure both oxygen consumption rate (OCR) and extracellular acidification rate (ECAR) to determine effects on oxidative phosphorylation (OXPHOS) and glycolysis simultaneously. The cells were then subjected to sequential exposure to various inhibitors of mitochondrial functional to assess cellular metabolism.

A positive mitochondrial active compound is determined when there is a change in OCR or ECAR in the absence of cytotoxicity. Cytotoxicity was determined when both oxidative phosphorylation (OCR) and glycolysis (ECAR) were inhibited.

OCR is a measurement of oxygen content in extracellular media. Changes in OCR indicate effects on mitochondrial function, and can be bi-directional. A decrease is due to an inhibition of mitochondrial respiration, whilst an increase may indicate an uncoupler, in which respiration is not linked to energy production.

$$OCR = \frac{\text{compound } OCR - \text{non mitochondrial } OCR}{\text{basal } OCR - \text{non mitochondrial } OCR}$$

ECAR is the measurement of extracellular proton concentration (pH). An increase in signal means an increase in rate in number of pH ions (Thus decreasing pH value), and seen as an increase in glycolysis. Expressed as a fraction of basal control (rate prior to addition of compound).

$$ECAR = \frac{\text{compound } ECAR}{\text{basal } ECAR}$$

Reverse capacity is the measured ability of cells to respond to an increase in energy demand, a reduction indicates mitochondrial dysfunction. This measurement demonstrates how close the bioenergic limit the cell is.

$$OCR = \frac{FCCP \ OCR - \text{non mitochondrial } OCR}{\text{basal } OCR - \text{non mitochondrial } OCR}$$

The Mitochondrial Stress Test is a series of sequential additions of compounds to the cells to assess a bioenergetics profile, and effects of test compounds on parameters such as proton leak and research capacity. This was used to assist in understanding potential mechanisms of mitochondrial toxicity. For example, it involves the addition of the follow compounds in this order:

Oligomycin is a known inhibitor of ATP synthase, and prevents the formation of ATP. This provides a measurement of the amount of oxygen consumption related to ATP production and ATP turnover. The addition of Oligomycin results in a decrease in OCR under normal conditions, and residual OCR is related to the natural proton leak.

Carbonyl cyanide 4-(trifluoromethoxy)phenylhydrazine (FCCP) is a protonphore, and is a known uncoupler of oxygen consumption from ATP production. This allows the maximum achievable transfer of electrons and oxygen consumption rate, and provides a measurement of reserve capacity.

Rotenone and antimycin A are known inhibitors of complex I and III of the electron transport chain, respectively. This inhibits electron transport completely, and any residual oxygen consumption is due to non-mitochondrial activity via oxygen requiring enzymes.

| Peptide Number | Peptide Sequence |
|---|---|
| I-1 | (D-Arg)(L-Dmt)(L-Lys)(L-Phe)-NH$_2$ |
| I-2 | (D-Arg)(L-Dmt)(L-Orn)(L-Phe)-NH$_2$ |
| I-3 | (D-Arg)(L-Tyr)(L-Orn)(L-Phe)-NH$_2$ |
| I-4 | (D-Orn)((L-Dmt)(L-Orn)(L-Phe)-NH$_2$ |
| I-5 | (D-Orn)(L-Tyr)(L-Orn)(L-Phe)-NH$_2$ |
| I-6 | (D-Lys)(L-Dmt)(L-Lys)(L-Phe)-NH$_2$ |
| I-7 | (D-Lys)(L-Dmt)(L-Orn)(L-Phe)-NH$_2$ |
| I-8 | (D-Lys)(L-Tyr)(L-Orn)(L-Phe)-NH$_2$ |
| I-9 | (D-Arg)(L-Dmt)(L-Lys)(L-Tyr)-NH$_2$ |
| I-10 | (D-Arg)(L-Dmt)(L-Orn)(L-Tyr)-NH$_2$ |
| I-11 | (L-Phe)(L-Lys)(L-Dmt)(D-Arg)-NH$_2$ |
| I-12 | (L-Phe)(L-Orn)(L-Dmt)(D-Arg)-NH$_2$ |
| I-13 | (L-Phe)(L-Orn)(L-Dmt)(D-Orn)-NH$_2$ |
| I-14 | (L-Phe)(L-Orn)(L-Tyr)(D-Arg)-NH$_2$ |
| I-15 | (L-Phe)(L-Orn)(L-Tyr)(D-Orn)-NH$_2$ |
| I-16 | (D-Phe)(D-Orn)(D-Tyr)(L-Arg)-NH$_2$ |
| I-17 | (D-Phe)(D-Orn)(D-Tyr)(L-Orn)-NH$_2$ |
| I-18 | (D-Phe)(D-Lys)(D-Dmt)(L-Arg)-NH$_2$ |
| I-19 | (D-Phe)(D-Orn)(D-Dmt)(L-Arg)-NH$_2$ |
| I-20 | (D-Phe)(D-Orn)(D-Dmt)(L-Orn)-NH$_2$ |
| I-21 | (D-Arg)(L-Leu)(L-Lys)(L-Phe)-NH$_2$ |
| I-22 | (D-Arg)(L-Phe)(L-Lys)(L-Phe)-NH$_2$ |
| I-23 | (D-Arg)(L-Leu)(L-Orn)(L-Phe)-NH$_2$ |
| I-24 | (D-Arg)(L-Leu)(L-Orn)(L-Leu)-NH$_2$ |
| I-25 | (D-Lys)(L-Leu)(L-Orn)(L-Leu)-NH$_2$ |
| I-26 | (D-Orn)(L-Leu)(L-Orn)(L-Leu)-NH$_2$ |
| I-27 | (D-Orn)(L-Phe)(L-Orn)(L-Phe)-NH$_2$ |
| I-28 | (L-Phe)(L-Lys)(L-Leu)(D-Arg)-NH$_2$ |
| I-29 | (L-Phe)(L-Lys)(L-Phe)(D-Arg)-NH$_2$ |
| I-30 | (L-Phe)(L-Orn)(L-Leu)(D-Arg)-NH$_2$ |
| I-31 | (L-Phe)(L-Orn)(L-Leu)(D-Orn)-NH$_2$ |
| I-32 | (L-Leu)(L-Orn)(L-Leu)(D-Orn)-NH$_2$ |
| I-33 | (L-Phe)(L-Orn)(L-Phe)(D-Orn)-NH2 |
| I-34 | (D-Phe)(D-Lys)(D-Leu)(L-Arg)-NH$_2$ |
| I-35 | (D-Phe)(D-Orn)(D-Leu)(L-Arg)-NH$_2$ |
| I-36 | (D-Phe)(D-Orn)(D-Leu)(L-Orn)-NH$_2$ |
| I-37 | (D-Leu)(D-Orn)(D-Leu)(L-Orn)-NH$_2$ |
| I-38 | (D-Phe)(D-Orn)(D-Phe)(L-Orn)-NH$_2$ |
| I-39 | (D-Phe)(D-Orn)(D-Tyr)(D-Orn)-NH$_2$ |

TABLE A

| Peptide | OCR ↑↓ | OCR MEC (µM) | OCR AC$_{50}$ (µM) | Reserve Capacity ↑↓ | Reserve Capacity MEC (µM) | Reserve Capacity AC$_{50}$ (µM) | ECAR ↑↓ | ECAR MEC (µM) | ECAR AC$_{50}$ (µM) | Potential Mechanism |
|---|---|---|---|---|---|---|---|---|---|---|
| I-1 (1) | | NR | NR | | NR | NR | | NR | NR | No effect |
| I-1 (2) | | NR | NR | ↑ | 90.3 | >100 | ↓ | 14.3 | >100 | Other |
| I-3 (1) | | NR | NR | ↑ | 48.5 | >100 | | NR | NR | Other |
| I-3 (2) | | NR | NR | ↑ | 85.3 | >100 | | NR | NR | Other |
| I-5 (1) | | NR | NR | ↑ | 15.8 | >100 | | NR | NR | Other |
| I-5 (2) | | NR | NR | ↓ | <0.1 | 0.954 | | NR | NR | Other |
| I-13 (1) | | NR | NR | ↑ | 13.4 | 81.9 | | NR | NR | Other |
| I-13 (2) | | NR | NR | ↓ | 0.167 | 4.72 | | NR | NR | Other |
| I-4 | | NR | NR | | NR | NR | | NR | NR | No effect |
| I-6 | | NR | NR | ↑ | 50.3 | >100 | | NR | NR | Other |
| I-8 | | NR | NR | ↑ | 79.7 | >100 | | NR | NR | Other |
| I-9 | | NR | NR | | NR | NR | | NR | NR | No effect |
| I-14 | | NR | NR | | NR | NR | | NR | NR | No effect |
| I-15 | | NR | NR | ↑ | 64.7 | >100 | | NR | NR | Other |
| I-16 | | NR | NR | ↑ | 84.5 | >100 | | NR | NR | Other |
| I-17 | | NR | NR | ↑ | 48.8 | >100 | | NR | NR | Other |
| I-2 | | NR | NR | | NR | NR | | NR | NR | No effect |
| I-7 | | NR | NR | | NR | NR | | NR | NR | No effect |

TABLE A-continued

| | OCR | | | Reserve Capacity | | | ECAR | | Potential Mechanism |
|---|---|---|---|---|---|---|---|---|---|
| Peptide | ↑↓ | MEC (µM) | AC$_{50}$ (µM) | ↑↓ | MEC (µM) | AC$_{50}$ (µM) | ↑↓ | MEC (µM) | AC$_{50}$ (µM) | |
| I-10 | | NR | NR | | NR | NR | | NR | NR | No effect |
| I-11 | | NR | NR | | NR | NR | | NR | NR | No effect |
| I-12 | | NR | NR | | NR | NR | | NR | NR | No effect |
| I-21 | | NR | NR | ↑ | 62.5 | >100 | | NR | NR | Other |
| I-22 | | NR | NR | ↑ | 100 | >100 | | NR | NR | No effect |
| I-23 | | NR | NR | ↑ | 65.9 | >100 | | NR | NR | Other |
| I-24 | | NR | NR | ↑ | 33.8 | >100 | | NR | NR | Other |
| I-25 | | NR | NR | | NR | NR | | NR | NR | No effect |
| I-26 | | NR | NR | | NR | NR | | NR | NR | No effect |
| I-27 | | NR | NR | | NR | NR | | NR | NR | No effect |
| I-28 | | NR | NR | ↓ | <0.1 | 1.28 | | NR | NR | Other |
| I-29 | | NR | NR | ↓ | 0.203 | 4.17 | | NR | NR | Other |
| I-30 | | NR | NR | | NR | NR | | NR | NR | No effect |
| I-31 | | NR | NR | | NR | NR | | NR | NR | No effect |
| I-32 | | NR | NR | ↓ | 0.277 | 9.32 | | NR | NR | Other |
| I-33 | | NR | NR | | NR | NR | | NR | NR | No effect |
| I-34 | | NR | NR | ↓ | <0.1 | 0.957 | | NR | NR | Other |
| I-35 | | NR | NR | ↓ | <0.1 | 5.28 | | NR | NR | Other |
| I-36 | | NR | NR | ↓ | 0.139 | 6.45 | | NR | NR | Other |
| I-37 | ↓ | 143 | >100 | ↓ | <0.1 | 1.11 | | NR | NR | Other |
| I-38 | | NR | NR | | NR | NR | | NR | NR | No effect |
| I-17 (2) | | NR | NR | ↑ | 69.1 | >100 | | NR | NR | Other |
| Succinate | ↑ | 74.8 | >100 | ↑ | 62.5 | >100 | | NR | NR | Uncoupler |
| Succinate + β-OHB | ↑ | 71.3 | >100 | ↑ | 30.3 | >100 | | NR | NR | Uncoupler |
| Succinate + β-OHB + I-17 | | NR | NR | ↑ | 28.9 | >100 | | NR | NR | Other |
| β-OHB | | NR | NR | ↑ | 53.0 | >100 | | NR | NR | Other |
| Rotenone | ↓ | <0.003 | 0.0138 | ↓ | <0.003 | 0.00349 | ↑ | 0.00325 | 0.496 | ETC inhibitor |

TABLE B

| | OCR | | | Reserve Capacity | | | ECAR | | Potential Mechanism |
|---|---|---|---|---|---|---|---|---|---|
| Peptide | ↑↓ | MEC (µM) | AC$_{50}$ (µM) | ↑↓ | MEC (µM) | AC$_{50}$ (µM) | ↑↓ | MEC (µM) | AC$_{50}$ (µM) | |
| I-17$^{NTA/*}$ | | NR | NR | | NR | NR | ↓ | 14.1 | >100 | No effect |
| I-17* | | NR | NR | | NR | NR | ↓ | 20.9 | >100 | No effect |
| I-17$^{NTA}$ | | NR | NR | | NR | NR | ↓ | 31.8 | >100 | No effect |

TABLE C

| | OCR | | | Reserve Capacity | | | ECAR | | Potential Mechanism |
|---|---|---|---|---|---|---|---|---|---|
| Peptide | ↑↓ | MEC (µM) | AC$_{50}$ (µM) | ↑↓ | MEC (µM) | AC$_{50}$ (µM) | ↑↓ | MEC (µM) | AC$_{50}$ (µM) | |
| I-39(1) | | NR | NR | ↑ | 92.4 | >100 | ↓ | 30.1 | >100 | Other |

TABLE D

| | OCR | | | Reserve Capacity | | | ECAR | | Potential Mechanism |
|---|---|---|---|---|---|---|---|---|---|
| Peptide | ↑↓ | MEC (µM) | AC$_{50}$ (µM) | ↑↓ | MEC (µM) | AC$_{50}$ (µM) | ↑↓ | MEC (µM) | AC$_{50}$ (µM) | |
| I-39(2) | | NR | NR | ↑ | 67.6 | >100 | ↓ | 15.3 | >100 | Other |
| I-39(3) | | NR | NR | ↑ | 77.3 | >100 | ↓ | 21.2 | >100 | Other |

Example 3

Functional Mitochondrial Toxicity Assay
(GM01299 Propionic Acidemia Human Cell Line)

The present Example interrogates the two major energy producing pathways in the cell, mitochondrial respiration and glycolysis. A GM01299 propionic acidemia human cell line was dosed with test compound I-17 using the general protocol outlined in Example 2 above.

TABLE E

| | OCR | | | Reserve Capacity | | | ECAR | | Potential Mechanism |
|---|---|---|---|---|---|---|---|---|---|
| Peptide | ↑↓ | MEC (µM) | AC$_{50}$ (µM) | ↑↓ | MEC (µM) | AC$_{50}$ (µM) | ↑↓ | MEC (µM) | AC$_{50}$ (µM) | |
| I-17 | | NR | NR | ↑ | 18.0 | >100 | ↓ | 84.1 | >100 | Other |
| Succinate | | NR | NR | ↑ | 38.2 | >100 | | NR | NR | Other |
| Succinate + β-OHB | | NR | NR | ↑ | 40.4 | >100 | | NR | NR | Other |
| Succinate + β-OHB + I-17 | | NR | NR | ↑ | 7.35 | 13.9 | | NR | NR | Other |
| β-OHB | | NR | NR | ↑ | 25.3 | >100 | ↓ | 89.8 | >100 | Other |

Example 4

Functional Mitochondrial Toxicity Assay
(GM05162 Duchenne Muscular Dystrophy Human Cell Line)

The present Example interrogates the two major energy producing pathways in the cell, mitochondrial respiration and glycolysis. A GM05162 Duchenne muscular dystrophy human cell line was dosed with test compound I-17 using the general protocol outlined in Example 2 above.

TABLE F

| | OCR | | | Reserve Capacity | | | ECAR | | Potential Mechanism |
|---|---|---|---|---|---|---|---|---|---|
| Peptide | ↑↓ | MEC (µM) | AC$_{50}$ (µM) | ↑↓ | MEC (µM) | AC$_{50}$ (µM) | ↑↓ | MEC (µM) | AC$_{50}$ (µM) | |
| I-17 | | NR | NR | ↑ | 0.788 | >100 | ↓ | 76.8 | >100 | Other |
| Succinate | | NR | NR | | NR | NR | ↑ | 0.179 | 2.91 | Other |
| Succinate + β-OHB | | NR | NR | ↑ | 0.145 | >100 | | NR | NR | Other |
| Succinate + β-OHB + I-17 | | NR | NR | ↑ | 0.300 | >100 | ↓ | 46.6 | >100 | Other |
| β-OHB | | NR | NR | ↑ | 1.15 | 69.5 | | NR | NR | Other |

Example 5

Functional Mitochondrial Toxicity Assay (GM16548 Rett Syndrome Human Cell Line)

The present Example interrogates the two major energy producing pathways in the cell, mitochondrial respiration and glycolysis. A GM16548 Rett syndrome human cell line was dosed with test compound I-39 using the general protocol outlined in Example 2 above.

TABLE G

| Peptide | OCR ↑↓ | OCR MEC (µM) | OCR $AC_{50}$ (µM) | Reserve Capacity ↑↓ | Reserve Capacity MEC (µM) | Reserve Capacity $AC_{50}$ (µM) | ECAR ↑↓ | ECAR MEC (µM) | ECAR $AC_{50}$ (µM) | Potential Mechanism |
|---|---|---|---|---|---|---|---|---|---|---|
| I-39 | | NR | NR | ↑ | 60.2 | >100 | | NR | NR | Other |
| Succinate | | NR | NR | ↑ | 72.3 | >100 | | NR | NR | Other |
| Succinate + β-OHB | ↑ | 2.80 | 10.7 | | NR | NR | | NR | NR | Other |
| Succinate + β-OHB + I-39 | | NR | NR | | NR | NR | ↓ | 25.8 | >100 | No effect |
| β-OHB | | NR | NR | ↑ | 23.1 | 72.2 | | NR | NR | Other |

Example 6

Functional Mitochondrial Toxicity Assay (GM01061 Huntington Disease Human Cell Line)

The present Example interrogates the two major energy producing pathways in the cell, mitochondrial respiration and glycolysis. A GM01061 Huntington Disease human cell line was dosed with test compound I-39 using the general protocol outlined in Example 2 above.

TABLE H

| Peptide | OCR ↑↓ | OCR MEC (µM) | OCR $AC_{50}$ (µM) | Reserve Capacity ↑↓ | Reserve Capacity MEC (µM) | Reserve Capacity $AC_{50}$ (µM) | ECAR ↑↓ | ECAR MEC (µM) | ECAR $AC_{50}$ (µM) | Potential Mechanism |
|---|---|---|---|---|---|---|---|---|---|---|
| I-39 | | NR | NR | | NR | NR | | NR | NR | No effect |
| Succinate | | NR | NR | | NR | NR | | NR | NR | No effect |
| Succinate + β-OHB | ↑ | 0.641 | 13.0 | | NR | NR | ↓ | 38.6 | >100 | Other |
| Succinate + β-OHB + I-39 | | NR | NR | | NR | NR | ↓ | 26.5 | 38.0 | No effect |
| β-OHB | | NR | NR | ↑ | 81.1 | >100 | | NR | NR | Other |

Example 7

Efficacy of Compound I-17 on Progressive Muscular Dystrophy in MDX Mice

One objective of this study was to investigate the efficacy of test compounds on progressive muscular dystrophy in MDX mice. Mice were dosed with compounds starting at 5 weeks of age until 17 weeks of age. At 16 weeks of age, the mice were tested for fine motor kinematics. At 17 weeks of age, quantitative muscular T2 MRI was performed to evaluate oedema and tissue damage. At the endpoint of 17 weeks of age, plasma was collected for creatine kinase (CK) measurements. This animal model demonstrated that MDX mice treated with I-17 showed a reduction in fibrosis as measured by MRI as compared to vehicle treated MDX mice.

Materials and Methods

All animal experiments were carried out according to the National Institute of Health (NIH) guidelines for the care and use of laboratory animals, and approved by the National Animal Experiment Board, Finland.

A total of 30 MDX mice (C57Bl/10ScSn-Dmd$^{mdx}$/J, #001801) and 10 C57 male mice bred and genotyped by JAX Labs, USA, were used for the experiment. Animals arrived at 5 weeks of age. Animals were housed at a standard temperature (22±1° C.) and in a light-controlled environment (lights on from 7 am to 9 pm) with ad libitum access to food and water.

Treatment Groups

The following treatment groups were used:
Group 1: 10 C57 male mice treated with 250 ul of vehicle (0.9% normal saline) solution (s.c., QD).
Group 2: 10 MDX male mice treated with 250 ul of vehicle (0.9% normal saline)solution (s.c., QD).
Group 3: 10 MDX male mice treated with 250 ul of peptide solution (0.3 mg/ml) (s.c., QD).

Schematic of Study Paradigm

Figure 3:
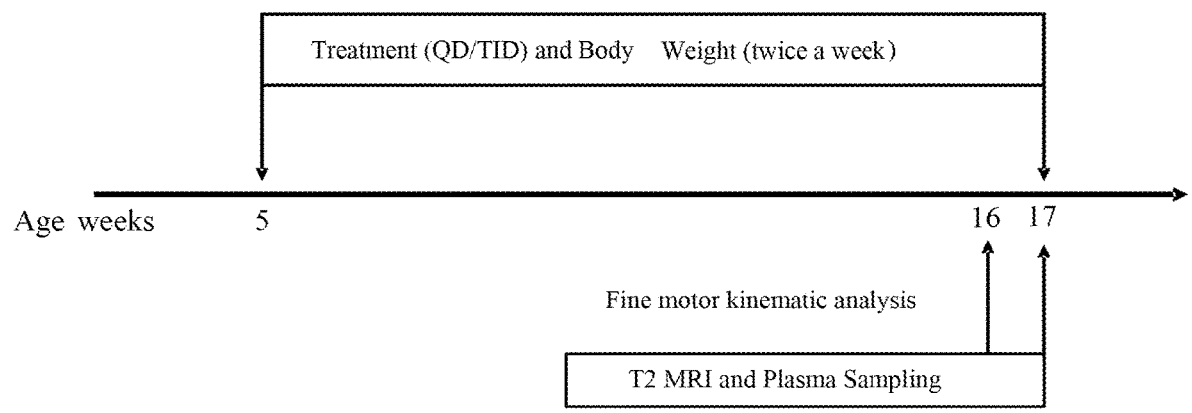
FIG. 3. Schematic of the study paradigm described in Example 7.
Figure 4:
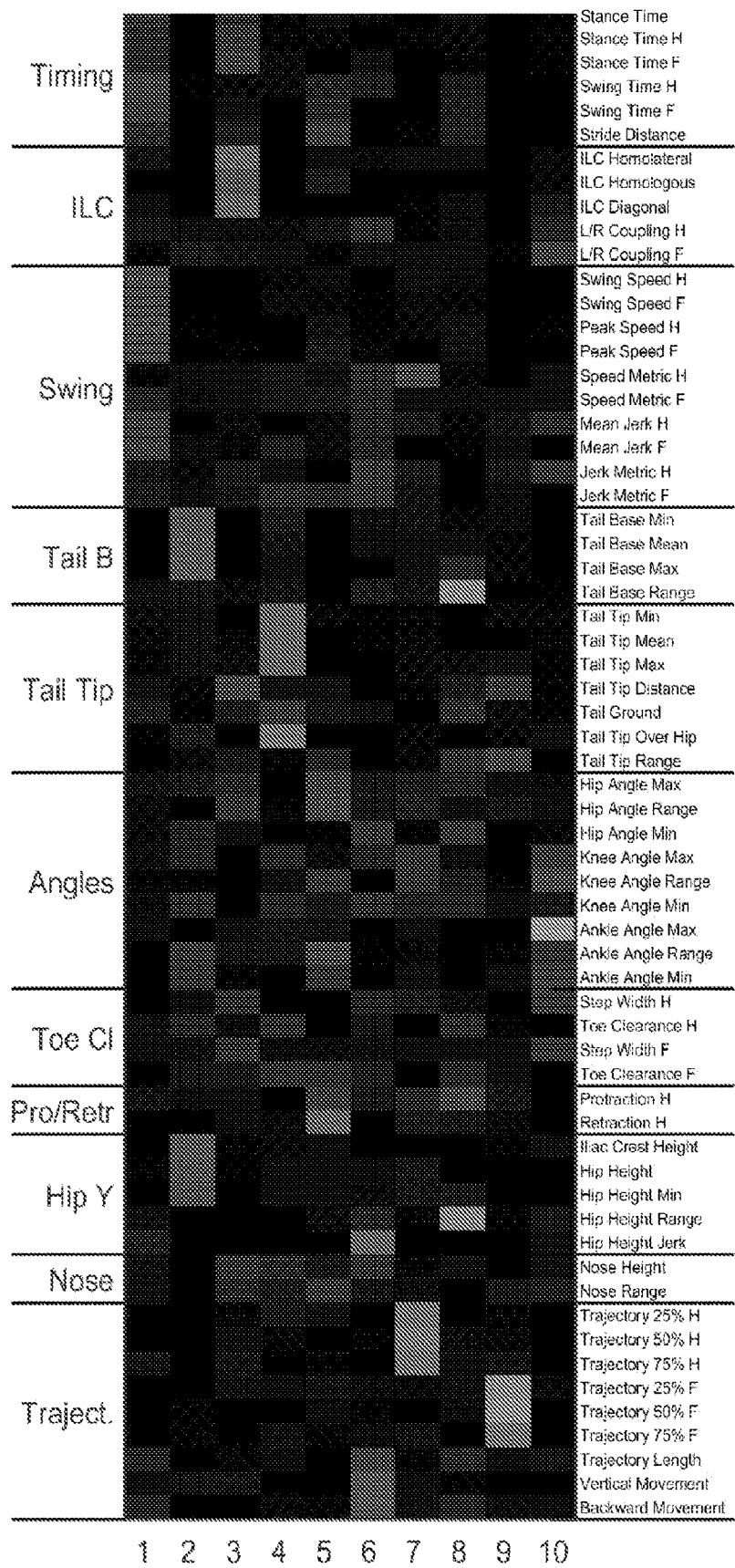
FIG. 4. Correlation heat map describing degree of correlation for each walking parameter in the data set. Red color means positive correlation, while blue means negative and black means no correlation.

A schematic of the study paradigm is depicted in FIG. 3. All mice were housed in groups of up to 4-5 per cage, in a temperature (22±1° C.) and humidity (30-70%) controlled environment with a normal light-dark cycle (7:00-20:00). All mice were housed in cages with clean bedding covering the ground that was changed as frequently as needed to provide the animals with dry bedding. This basic environment was enriched with the addition of play tunnels (amber color, certified, transparent, BioServ Product# K3323), wooden nesting material, and wooden chewing sticks. Food (Purina Lab Diet 5001) and water were available ad libitum to the mice in their home cages.

Animals were monitored daily by laboratory personnel. In case the general health status of an animal was significantly worsened, the mouse was sacrificed by an overdose of $CO_2$ and decapitated. Definitions of acceptable endpoints included: no spontaneous movements and inability to drink or eat in 24-h observation period, massive bleeding, spontaneous inflammation, missing anatomy, swelling or tumors larger than 20 mm, and inability to right itself in 20 second period.

Body weight was measured twice a week.

Fine Motor Kinematic Analysis

The fine motor skills were measured in the MotoRater (TSE Systems, Homburg, Germany) using walking mode at 16 weeks of age. A few days before the test sessions, under light isoflurane anesthesia the fur of the limbs was removed. On the day of testing, the mice were marked in appropriate points of body, such as joints of limbs and parts of tail to ease the data analysis process. The movement data was captured using a high speed camera (300 frames/second) from three different dimensions, from below and both sides. The captured videos of each mouse were first converted to SimiMotion software to track the marked points of body to have the raw data i.e. the movement of the different body points in coordinates in relation to the ground, and each of the three dimensions were correlated. Different gait patterns and movements were analyzed using a custom made automated analysis system. The analyzed parameters included e.g.: 1) general gait pattern parameters (stride time and speed, step width, stance and swing time during a stride, interlimb coordination), 2) body posture and balance (toe clearance, iliac crest and hip height, hind limb protraction and retraction, tail position and movement), and 3) fine motor skills (swing speed during a stride, jerk metric during swing phase, angle ranges and deviations of different joints, vertical and horizontal head movement).

T2 MRI

MRI analysis was performed in a horizontal 11.7 T magnet with bore size 160 mm equipped with a gradient set capable of max. gradient strength 750 mT/m and interfaced to a Bruker Avance III console (Bruker Biospin GmbH, Ettlingen, Germany). A volume coil (Bruker Biospin GmbH, Ettlingen, Germany) was used for transmission and a surface phased array coil for receiving (Rapid Biomedical GmbH, Rimpar, Germany). Isoflurane -anesthetized mice were fixed to a head holder and positioned in the magnet bore in a standard orientation relative to gradient coils.

T2 mapping was achieved using MSME sequence with TR of 2150 ms, 7 echo times in 10.5 ms intervals between range of 10.5-73.5 ms, 25 0.6 mm thick slices and FOV/matrix of 25.6×19.2 mm2/256×192 providing 100 microns in-plane resolution. Hyperintensity regions were quantified based on T2 MRI maps in MATLAB environment and T2 values (ms) in total muscle groups (tibialis anterior, gastrocnemius, medial compartments). Percentages of hyperintensity volume for muscle groups were provided.

Statistical Analysis

All values were presented as mean±standard error of mean (SEM), and differences were considered to be statistically significant at the $p<0.05$ level. Statistical analysis was performed using StatsDirect statistical software. Differences between MDX treatment groups were analyzed by using 1-way-ANOVA followed by Dunnet's test (comparison to the MDX vehicle group). Differences between vehicle treated WT and MDX mice were analyzed using Student's t-test.

Results:

Body Weight & Mortality

There were no differences in body weight between the MDX treatment groups. Body weight was significantly increased in vehicle treated MDX mice compared to vehicle treated C57 mice on age weeks 5-17 ($p<0.05$).

One MDX mouse from Veh (s.c.)+Veh (p.o.) was found dead. Autopsy did not reveal anything abnormal in this mouse.

Fine Motor Kinematics

Gait characteristics and fine motor skills of the mice were evaluated at 16 weeks of age. Mice were tested for their fine motor capabilities and gait properties using the walking mode. Data were analyzed for altogether 91 distinctive parameters, as well as using principal component analysis for all parameters together (PPCA).

T2 MRI

Figure 5:
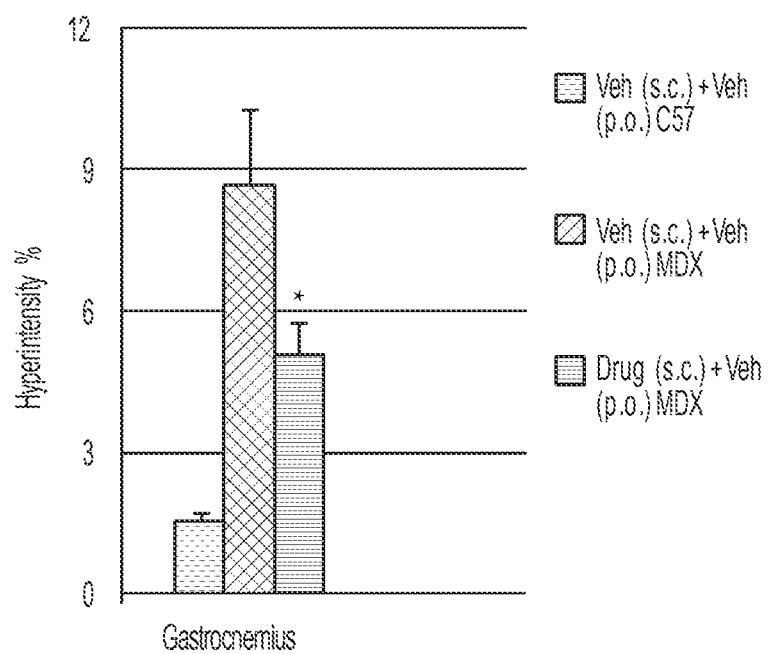
FIG. 5. Graph depicting higher gastrocnemius muscle hyperintensity % values in vehicle treated MDX mice as compared to vehicle treated C57 mice and lower gastrocnemius muscle hyperintensity in the drug-treated MDX mice as compared to the vehicle-treated MDX mice. The asterisk (*) indicates p<0.05 as compared to the vehicle-treated MDX group.

Gastrocnemius muscle hyperintensity % value was decreased in Drug (s.c.) group compared to Veh (s.c.) group ($p<0.05$). Hyperintensity % values were higher in vehicle treated MDX mice compared to vehicle treated C57 mice ($p<0.05$) (FIG. 5).

Example 8

Determination of the Stability of a Test Compound in Simulated Gastric Fluid

Experimental Procedure:

The study was carried out in simulated gastric fluid (SGF). SGF was prepared by dissolving 2.0 g of NaCl and 3.2 g of purified pepsin (derived from porcine stomach mucosa) in 7 mL of 10 N HCl and sufficient water to make 1000 mL. The pH was adjusted to pH 1.2. A DMSO stock was first prepared for I-17. Aliquots of the DMSO solution were dosed into 0.5 mL of matrix, which had been pre-warmed to 37° C., at a final I-17 concentration of 1 µM. The vials were kept in a benchtop Thermomixer® for the duration of the experiment. A separate tube was dosed for each time point in each matrix. At the appropriate times (0, 15, 30, 60, and 120 minutes), 1.0 mL of acetonitrile (ACN) containing internal standard was added directly to a single tube. Samples were mixed and then immediately stored at 4° C. until the end of the experiment. After the final time point was sampled, the tubes were centrifuged at 3,000 rpm for 10 minutes. Aliquots of the supernatant were removed, diluted with water, and analyzed by LC-MS/MS.

Experimental Results:

TABLE I

| Compound | Matrix | 0 min | 15 min | 30 min | 60 min | 120 min | Half-life (min) |
| --- | --- | --- | --- | --- | --- | --- | --- |
| I-17 | SGF | 100 | 92 | 99 | 101 | 90 | >120 |

Analytical Method:
Liquid Chromatography
Column: Waters ACQUITY UPLC BEH Phenyl 30×2.1 mm, 1.7 mm
M.P. Buffer: 25 mM ammonium formate buffer, pH 3.5
Aqueous Reservoir (A): 90% water, 10% buffer
Organic Reservoir (B): 90% acetonitrile, 10% buffer
Flow Rate: 0.7 mL/minute
Gradient Program:

| Time (min) | % A | % B |
| --- | --- | --- |
| 0.0 | 100 | 0 |
| 0.65 | 0 | 100 |

-continued

| Time (min) | % A | % B |
|---|---|---|
| 0.75 | 0 | 100 |
| 0.8 | 100 | 0 |
| 1.0 | 100 | 0 |

Total Run Time: 1.0 minutes
Autosampler: 5 µL Injection Volume
Wash1: water/methanol/2-propanol:1/1/1; with 0.2% formic acid
Wash2: 0.1% formic acid in water
  Mass Spectrometer
Instrument: PE SCIEX API 4000
Interface: Turbo Ionspray
Mode: Multiple reaction monitoring
Method: 1.0 minute duration
Settings:

| Compound | Q1/Q3 | DP | EP | CE | CXP | IS | TEM | CAD | CUR | GS1 | GS2 |
|---|---|---|---|---|---|---|---|---|---|---|---|
| I-17 | +556.5/278.0 | 95 | 10 | 29 | 20 | 5500 | 500 | 7 | 30 | 50 | 50 |

Example 9

Oral Bioavailability of I-17 in Male Sprague-Dawley Rats

In this study, the oral bioavailability of I-17 was evaluated in male Sprague-Dawley rats. I-17 was dosed by oral (PO) route of administration at 10 mg/kg. Blood samples were collected up to 6 hours postdose, and plasma concentrations of I-17 were determined by LC-MS/MS. Pharmacokinetic parameters were determined using WinNonlin (v6.3).

Following PO dosing of I-17, average $C_{max}$ was 295±47.6 ng/mL at a dose of 10 mg/kg. $T_{max}$ was observed at between 30 minutes and 1 hour post dosing. The average half life was 1.70 hours for the 10 mg/kg dose. The average oral bioavailability for I-17 was 1.96±0.198% at 10 mg/kg.

The dosing solutions were analyzed by LC-MS/MS. The dosing solutions were diluted into rat plasma and analyzed in triplicate. All concentrations are expressed as mg/mL of the free base. The nominal dosing level was used in all calculations.

TABLE J

Individual and Average Plasma Concentrations (ng/mL) and Pharmacokinetic Parameters for I-17 After Oral Administration at 10 mg/kg in Male Sprague-Dawley Rats
Oral (10 mg/kg)

| | Rat # | | | | |
|---|---|---|---|---|---|
| Time hr | 238 | 239 | 240 | Mean | SD |
| 0 (pre-dose) | BLOQ | BLOQ | BLOQ | ND | ND |
| 0.25 | 340 | 275 | 162 | 259 | 90.1 |
| 0.5 | 349 | 273 | 151 | 258 | 99.9 |
| 1.0 | 178 | 221 | 260 | 220 | 41.0 |
| 3.0 | 110 | 136 | 100 | 115 | 18.6 |
| 6.0 | 17.9 | 36.2 | 11.1 | 21.7 | 13.0 |
| Animal Weight (g) | 0.250 | 0.246 | 0.241 | 0.246 | 0.00451 |
| Volume Dosed (mL) | 2.50 | 2.46 | 2.41 | 2.46 | 0.0451 |
| $C_{max}$ (ng/mL) | 349 | 275 | 260 | 295 | 47.6 |
| $t_{max}$ (hr) | 0.500 | 0.250 | 1.00 | 0.583 | 0.382 |
| $t_{1/2}$ (hr) | 1.47 | 1.92 | ND[3] | 1.70 | ND |

TABLE J-continued

Individual and Average Plasma Concentrations (ng/mL) and Pharmacokinetic Parameters for I-17 After Oral Administration at 10 mg/kg in Male Sprague-Dawley Rats
Oral (10 mg/kg)

| | Rat # | | | | |
|---|---|---|---|---|---|
| Time hr | 238 | 239 | 240 | Mean | SD |
| $MRT_{last}$ (hr) | 1.75 | 2.01 | 1.76 | 1.84 | 0.146 |
| $AUC_{last}$ (hr · ng/mL) | 740 | 842 | 689 | 757 | 77.8 |
| $AUC_\infty$ (hr · ng/mL) | 778 | 942 | ND[3] | 860 | ND |
| Dose-normalized Values[1] | | | | | |
| $AUC_{last}$ (hr · kg · ng/mL/mg) | 74.0 | 84.2 | 68.9 | 75.7 | 7.78 |
| $AUC_{28}$ (hr · kg · ng/mL/mg) | 77.8 | 94.2 | ND[3] | 86.0 | ND |
| Bioavailability (%)[2] | 1.89 | 2.15 | 1.76 | 1.96 | 0.198 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (1 ng/mL);
[1]Dose-normalized by dividing the parameter by the nominal dose in mg/kg;
[2]Bioavailability determined by dividing the individual dose-normalized oral $AUC_{last}$ values by the average IV $AUC_{last}$ value;
[3]not determined because there was an insufficient number of data points trailing the $C_{max}$.

Example 10

Determination of the Exposure of I-17 After Intraduodenal Administration in Male Sprague-Dawley Rats In this study, the bioavailability of I-17 after intraduodenal dosing was evaluated in male Sprague-Dawley rats. I-17 was dosed by intraduodenal (ID) route of administration at 1 mg/kg. Blood samples were collected up to 6 hours post-dose, and plasma concentrations of I-17 were determined by LC-MS/MS. Pharmacokinetic parameters were determined using Phoenix WinNonlin (v6.4). Following ID dosing of I-17 at 1 mg/kg, the average $C_{max}$ was 143±35.6 ng/mL. The $t_{max}$ was observed between 15 and 30 minutes post dosing. The average half-life was 1.48 hours. The average exposure based on the $AUC_{last}$ was 142±39.3 hr*kg*ng/mL/mg, and the average intraduodenal bioavailability for I-17 was 3.63±1.00%.

TABLE K

Individual and Average Plasma Concentrations (ng/mL) and Pharmacokinetic Parameters for I-17 after Intraduodenal Administration at 1 mg/kg in Male Sprague-Dawley Rats
(1 mg/kg)

| Time (hr) | Rat # | | | Mean | SD |
| --- | --- | --- | --- | --- | --- |
| | 526 | 527 | 528 | | |
| 0 (pre-dose) | BLOQ | BLOQ | BLOQ | ND | ND |
| 0.083 | 103 | 91.1 | 118 | 104 | 13.5 |
| 0.25 | 85.7 | 136 | 182 | 135 | 48.2 |
| 0.5 | 112 | 116 | 162 | 130 | 27.8 |
| 1.0 | 17.0 | 17.0 | 21.0 | 18.3 | 2.31 |
| 3.0 | 7.79 | 15.3 | 14.1 | 12.4 | 4.03 |
| 6.0 | BLOQ | 1.53 | 3.53 | 2.53 | ND |
| Animal Weight (g) | 0.236 | 0.254 | 0.256 | 0.249 | 0.0110 |
| Volume Dosed (mL) | 1.18 | 1.27 | 1.28 | 1.24 | 0.0551 |
| $C_{max}$ (ng/mL) | 112 | 136 | 182 | 143 | 35.6 |
| $t_{max}$ (hr) | 0.500 | 0.250 | 0.250 | 0.333 | 0.144 |
| $t_{1/2}$ (hr) | ND[2] | 1.06 | 1.90 | 1.48 | ND |
| $MRT_{last}$ (hr) | 0.699 | 1.24 | 1.14 | 1.02 | 0.286 |
| $AUC_{last}$ (hr · ng/mL) | 102 | 145 | 180 | 142 | 39.3 |
| $AUC_{\infty}$ (hr · ng/mL) | ND[2] | 147 | 190 | 169 | ND |
| Bioavailability (%)[1] | 2.59 | 3.70 | 4.59 | 3.63 | 1.00 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;
ND: not determined;
BLOQ: below the limit of quantitation (0.5 ng/mL);
[1]Bioavailability determined by dividing the individual intraduodenal $AUC_{last}$ values by the average IV $AUC_{last}$ value from prior study (3923 hr * ng/mL);
[2]not determined because of a lack of quantifiable data points trailing the $C_{max}$.

Example 11

Stability of I-17 in Plasma and Whole Blood

The objective of this study was to determine the stability of I-17 in 1) human, rat, and dog plasma, 2) human, rat, and dog whole blood, and 3) simulated intestinal fluid containing various enzymes.
Experimental Procedure:
Studies were carried out in mixed-gender human plasma and whole blood, male Sprague-Dawley rat plasma and whole blood, and male Beagle dog plasma and whole blood. All plasma and blood were obtained from Bioreclamation and collected on sodium heparin. Plasma was adjusted to pH 7.4 prior to initiating the experiments. Studies were also carried out in simulated intestinal fluid in the presence of various enzymes. Simulated intestinal fluid was prepared by dissolving 6.8 g of monobasic potassium phosphate in 1.0 L of water. Aliquots of this solution were taken and the pH was adjusted to either 3.5 or 6.8. Individual enzymes were then spiked into aliquots for each experiment. A DMSO stock was first prepared for I-17. Aliquots of the DMSO solution were dosed into 1.5 mL of matrix, which had been pre-warmed to 37° C., at a final I-17 concentration of 1 µM. The vials were kept in a benchtop Thermomixer® for the duration of the experiment. Aliquots (200 µL) were taken at each time point (0, 15, 30, 60, and 120 minutes) and added to 96-well plates which had been pre-filled with 600 µL of acetonitrile containing internal standard. Samples were stored at 4° C. until the end of the experiment. After the final time point was sampled, the plate was mixed and then centrifuged at 3,000 rpm for 10 minutes. Aliquots of the supernatant were removed, evaporated under nitrogen to dryness, reconstituted with distilled water, and analyzed by LC-MS/MS. The peak area response ratio (PARR) to internal standard was compared to the PARR at time 0 to determine the percent remaining at each time point. Half-lives were calculated using GraphPad software, fitting to a single-phase exponential decay equation.

TABLE L

Stability of I-17

| Matrix | pH | Half life (min) |
| --- | --- | --- |
| Human plasma | 7.4 | >120 |
| Rat plasma | 7.4 | >120 |
| Dog plasm | 7.4 | >120 |
| Human blood | 7.4 | >120 |
| Rat blood | 7.4 | >120 |
| Dog blood | 7.4 | >120 |
| SIF + elastase | 3.5 | >120 |
| | 6.8 | >120 |
| SIF + pancreatin | 3.5 | >120 |
| | 6.8 | >120 |
| SIF + carboxypeptidase B | 3.5 | >120 |
| | 6.8 | >120 |
| SIF + carboxypeptidase A | 3.5 | >120 |
| | 6.8 | >120 |
| SIF + chymotrypsin | 3.5 | >120 |
| | 6.8 | >120 |
| SIF + trypsin | 3.5 | >120 |
| | 6.8 | >120 |

Example 12

Determination of the Bioavailability of I-17 Following Intravenous (IV), Oral (PO), and Intraduodenal (ID) Administration in Male Beagles In this study, the oral bioavailability of I-17 was evaluated in male beagle dogs. I-17 was dosed by intravenous (IV), intraduodenal (ID), and oral (PO) routes of administration at 1 mg/kg each. Blood samples were collected up to 24 hours post-dose, and plasma concentrations of I-17 were determined by LC-MS/MS. Pharmacokinetic parameters were determined using Phoenix WinNonlin (v6.4).

Following IV dosing at 1 mg/kg to fasted male beagle dogs, I-17 had an average half-life of 1.12±0.138 hours. Its average clearance rate was 0.129±0.00878 L/hr/kg. The average volume of distribution was 0.190±0.0120 L/kg.

Following ID dosing of I-17 (1 mg/kg) to fasted male beagle dogs, maximum plasma concentrations (average of 74.6±53.7 ng/mL) were observed between 1 and 2 hours post dosing. The average half-life could not be determined because the terminal elimination phase was not observed. The average exposure based on the $AUC_{last}$ was 173±126 hr*ng/mL. The average intraduodenal bioavailability for I-17 was 2.33±1.70%.

Following PO dosing of I-17 (1 mg/kg) to fasted male beagle dogs, maximum plasma concentrations (average of 124±48.9 ng/mL) were observed at 2 hours post dosing. The average half-life could not be determined because the terminal elimination phase was not observed. The average exposure based on the $AUC_{last}$ was 464±117 hr*ng/mL. The average oral bioavailability for I-17 was 6.25±1.57%.

Following PO dosing of I-17 (1 mg/kg) to fed male beagle dogs, maximum plasma concentrations (average of 51.6±54.9 ng/mL) were observed between 1 and 2 hours post dosing. The average half-life could not be determined because the terminal elimination phase was not observed; however, one dog had a half-life of 1.60 hours. The average exposure based on the $AUC_{last}$ was 160±186 hr*ng/mL. The average oral bioavailability for I-17 was 2.16±2.51%.

Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. A tetrameric peptide agent having sequence (D-Phe)(D-Orn)(D-Tyr)(L-Orn)-NH$_2$.

2. The tetrameric peptide agent of claim 1, wherein the peptide agent is in a salt form.

3. The tetrameric peptide agent of claim 2, wherein the salt form is a pharmaceutically acceptable salt form.

4. A pharmaceutical composition comprising the tetrameric peptide agent of claim 1 and a pharmaceutically acceptable excipient.

5. The pharmaceutical composition of claim 4, wherein the pharmaceutical composition is formulated for oral delivery.

6. A method of inhibiting mitochondrial respiration in a patient or in a biological sample, the method comprising a step of administering to said patient or contacting said biological sample with a peptide agent having sequence (D-Phe)(D-Orn)(D-Tyr)(L-Orn)-NH$_2$.

7. The method of claim 6, wherein the tetrameric peptide agent is in a salt form.

8. The method of claim 7, wherein the salt form is a pharmaceutically acceptable salt form.

9. The method of claim 6, wherein the tetrameric peptide agent is administered to said patient.

10. The method of claim 9, wherein the tetrameric peptide agent is administered in a pharmaceutical composition comprising a pharmaceutically acceptable excipient.

11. The method of claim 10, wherein the tetrameric peptide agent is administered orally.

12. The method of claim 9, wherein the patient has a disease, disorder, or condition is associated with mitochondrial dysfunction.

13. The method of claim 6, wherein the tetrameric peptide agent modulates mitochondrial function in a cell of the patient or biological sample.

14. The method of claim 13, wherein the tetrameric peptide agent increases mitochondrial reserve capacity in the cell.

* * * * *